(12) United States Patent
Matsumoto

(10) Patent No.: US 6,464,848 B1
(45) Date of Patent: *Oct. 15, 2002

(54) REFERENCE ELECTRODE, A BIOSENSOR AND A MEASURING APPARATUS THEREWITH

(75) Inventor: Toru Matsumoto, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/388,449

(22) Filed: Sep. 2, 1999

(30) Foreign Application Priority Data

Sep. 3, 1998 (JP) ............................. 10-249731

(51) Int. Cl.[7] ..................... G01N 27/333; G01N 27/327
(52) U.S. Cl. ................. 204/403.06; 204/435; 204/418; 204/290.01
(58) Field of Search ................... 204/435, 403, 204/416, 290 R, 418, 290.01, 403.06

(56) References Cited

U.S. PATENT DOCUMENTS 5,002,652 A * 3/1991 Nelson et al. ............... 204/412
5,378,344 A * 1/1995 Nakagawa ................... 204/418
6,280,587 B1 * 8/2001 Matsumoto ................. 204/403

FOREIGN PATENT DOCUMENTS

JP      5-223772      8/1993
JP      9-292361      11/1997

* cited by examiner

Primary Examiner—T. Tung
Assistant Examiner—Alex Noguerola
(74) Attorney, Agent, or Firm—Young & Thompson

(57) ABSTRACT

On an insulating substrate 1 is formed an electrode 2, on which is then formed a protection layer 3 consisting of a methacrylate-resin polyfluoroalcohol ester layer.

62 Claims, 15 Drawing Sheets

Potential of a hydrogen peroxide solution to a reference electrode (mV)

(a) Reference electrode according to this invention

Potential of a hydrogen peroxide solution to a reference electrode (mV)

(b) Conventional reference electrode (a)

A-A' CROSS SECTION

B-B' CROSS SECTION (b)　　　　　　　　　　(c)

(a)

B-B' CROSS SECTION     A-A' CROSS SECTION (b)                    (c)

(a)

(b) (c)

(a)

(b) (c)

B-B' CROSS SECTION    A-A' CROSS SECTION (b)                   (c)

REFERENCE ELECTRODE, A BIOSENSOR AND A MEASURING APPARATUS THEREWITH

REFERENCE TO RELATED APPLICATION AND INCORPORATION BY REFERENCE

This application is based on applications NO.HEI10-249731 filed in Japan, the content of which is incorporated hereinto by reference.

BACKGROUND OF THE INVENTION

1. Field of the Invention

This invention relates to a reference electrode used for electrochemically determining a particular chemical substance in a solution via a reaction such as an enzyme reaction as well as a biosensor therewith.

2. Description of the Related Art

The structure of a conventional reference electrode will be described with reference to FIG. 4, consisting of a cross-section and a plan view for a reference electrode disclosed in JP-A 9-182738. In FIG. 4(a), a polyimide layer PI1, an anode film M and a silver layer S are sequentially formed on a cathode film K. The silver layer S acts as a reference electrode, on which the polyimide layer PI2 is formed as a protection layer. It is described that instead of the polyimide layer PI2, a water-repelling photoresist may be formed as a protection layer. It is also described that such a protection layer can be formed on a reference electrode to extend the life of the electrode.

It has been, however, difficult to achieve a sufficiently long life for the above reference electrode because a part of the surface of the reference electrode is directly in contact with an electrolyte, so that silver chloride formed on the surface is likely to be dissociated in the electrolyte. According to our examination, a reference electrode having the above structure can usually operate for about 2 days while maintaining its initial performance.

When a water-repelling photoresist is used as a material for the protection layer in the above reference electrode, it may make a manufacturing process more complicated, leading to increase in a production cost. Thus, the technique has a room for improvement. It is because formation of a photoresist requires repeating exposure and development using a photolithography technique and forming an electrolyte injection port for injecting an electrolyte and open holes for removing bubbles generated during injection of the electrolyte.

Furthermore, there has been a problem that when the above reference electrode is applied to a biosensor, contaminants in a specimen adhere to its surface, causing reduction in sensitivity. The problem will be described.

A biosensor utilizes a catalytic enzyme to convert chemical substances in a solution into, e.g., hydrogen peroxide, which is then determined using an oxidation-reduction reaction. It is important to eliminate effects of interferent materials and contaminants for achieving stable properties and an extended life in a biosensor. An interferent material refers to a chemical substance which may affect the above oxidation-reduction reaction system to give a positive error in a measurement result, such as ascorbic acid and acetaminophen. A contaminant refers to a chemical substance which may be adsorbed by an electrode surface to give a negative error in a measurement result, such as albumin, urea, urea compounds and creatinine.

The above reference electrode according to the prior art, however, uses polyimide and/or a photoresist as a material for a protection layer and thus contaminants may easily attach to the surface of the protection layer. It has been, therefore, difficult to avoid reduction in sensitivity after a long-term use.

SUMMARY OF THE INVENTION

This invention provides a reference electrode comprising an electrode on an insulating substrate and a protection layer covering the electrode, said protection layer mainly consisting of a polymer in which a pendant group containing at least a fluoroalkylene block is attached to a non-fluorinated vinyl polymer.

That is, a reference electrode according to this invention consists of an electrode (electrode layer) on an insulating substrate and multiple layers having different functions on the electrode.

A reference electrode herein refers to an electrode as a standard for determining an electrode potential of a working electrode. The reference electrode of this invention may be suitably used for electrochemically determining a particular chemical substance in a solution using an enzyme electrode and thus suitably used for a part of, e.g., a biosensor.

In this invention, the polymer composing the protection layer has a pendant group comprising a fluoroalkylene block (fluoroalkylene unit). Such a configuration may prevent adhesion of contaminants such as proteins and urea compounds to provide a reference electrode exhibiting stable output properties even for a long-term use. The fluoroalkylene moiety may not contribute to dissolution into a washing agent such as non-fluorinated solvent and a surfactant, providing a reference electrode with good chemical resistance.

The polymer has a non-fluorinated vinyl polymer structure as a principal chain, which is highly adhesive to an electrode or another organic polymer layer formed on the electrode. It, therefore, does not cause a gap between the electrode or a layer such as an organic polymer layer formed on the electrode surface and the protection layer. Therefore, the electrode surface is not in contact with an electrode, which prevents metal composing the electrode portion from eluting into the electrode and leads to reduction in a time for washing the reference electrode.

In addition, its good adhesiveness to, e.g., the electrode may improve durability of the layered structure to provide a reference electrode resistant to deterioration due to a long-term use.

The polymer may have, in addition to the pendant group comprising a fluoroalkylene block, any other appropriate side chain or functional group; for example, a properly polar functional group such as —OH and —COOH groups may further improve adhesiveness to an electrode or another organic polymer layer formed on the electrode.

The protection layer in this invention may be formed as a homogeneous film by a convenient process such as dip-coating, spin-coating and spray-coating and may be suitable for mass production.

This invention also provides a reference electrode comprising an electrode on an insulating substrate and a protection layer covering the electrode, said protection layer mainly consisting of a polycarboxylic acid (A) fluoroalcohol ester.

This invention also provides a reference electrode comprising an electrode on an insulating substrate and a protection layer covering the electrode, said protection layer mainly consisting of a polycarboxylic acid (A) fluoroalcohol ester and a polycarboxylic acid (B) alkylalcohol ester.

This invention also provides a reference electrode comprising an electrode on an insulating substrate and a protection layer covering the electrode, said protection layer mainly consisting of a polycarboxylate comprising alkylalcohol ester and fluoroalcohol ester groups.

These reference electrodes consist of an electrode (electrode layer) on an insulating substrate and multiple layers having different functions on the electrode, characterized in that the protection layer is composed of a polymer having a particular structure.

In a reference electrode according to this invention, a fluoroalcohol polycarboxylate is used as a material for a protection layer. A fluoroalcohol polycarboxylate refers to a polycarboxylic acid, whose carboxyl groups are partially or totally esterified with a fluoroalcohol. A fluoroalcohol refers to an alcohol, at least one or all of whose hydrogen atoms are replaced with fluorine atom(s).

The protection layer material has a fluoroalcohol ester group, which may prevent adhesion of contaminants such as proteins and urea compounds, leading to a reference electrode exhibiting stable properties when used for a long term. The fluoroalcohol ester group makes the material insoluble in almost any non-fluorinated solvent or a washing agent such as a surfactant, to give a reference electrode with an improved chemical resistance.

The reference electrode of this invention has a protection layer comprising a polymer having a principal chain of a polycarboxylic acid, to which a fluoroalcohol is attached via an ester group. It, therefore, can improve adhesiveness to an electrode or another organic polymer layer formed on the electrode and prevent causing a gap between the electrode or the organic polymer layer and the protection layer. Therefore, the electrode surface is not in contact with an electrode, which prevents metal composing the electrode portion from eluting into the electrode and leads to reduction in a time for washing the reference electrode.

In addition, its good adhesiveness to, e.g., the electrode may improve durability of the layered structure to provide a reference electrode resistant to deterioration due to a long-term use.

The polymer may have, in addition to the fluoroalcohol ester group, any other appropriate functional group to the principal chain; a properly polar functional group may further improve adhesiveness to another organic polymer layer such as an adjacent electrode or a layer such as an organic polymer layer formed on the electrode.

When a protection layer comprises (a) a polycarboxylic acid (A) fluoroalcohol ester and a polycarboxylic acid (B) alkylalcohol ester or (b) a polycarboxylate having an alkylalcohol ester and a fluoroalcohol ester groups, high temperature stability may be improved, in addition to the above effects. A reference electrode or a biosensor therewith may be sometimes stored or used at a relatively higher temperature (for example, ca. 40° C.). When used for measurement after leaving at a higher temperature, sensitivity of a conventional reference electrode has often varied significantly, compared to measurement before exposure to the higher temperature. On the other hand, a reference electrode or biosensor comprising the above protection layer little varies in its sensitivity even after exposure to a higher temperature.

In a reference electrode of this invention as described above, an electrode and a protection layer may be formed in direct contact with each other or another layer may intervene these layers. For example, a binding layer mainly consisting of a silane-coupling agent is disposed between the electrode and the protection layer.

The protection layer may be formed as a homogeneous film by a convenient process such as dipping, spin-coating and spray coating and may be suitable for mass production.

This invention also provides a biosensor using the above reference electrode. The biosensor has a protection layer comprising the polymer having the above particular structure on the reference electrode surface. It, therefore, may be excellent in long-term stability and may be used under a wide range of measuring conditions.

This invention also relates to a variety of measuring apparatus using the above biosensor. Specifically, this invention provides a measuring apparatus comprising the above biosensor and a data indicator indicating an electric signal from the biosensor.

This invention also provides a measuring apparatus comprising the above biosensor, an electrochemical measuring circuit receiving an electric signal from the biosensor, a data processor calculating a measured value based on the electric signal and a data indicator indicating the measured value.

These measuring apparatuses may realize excellent long-term stability and may be used under wide ranges of measuring conditions because of their biosensor having a particular structure of working electrode. They are also easily operated even by an unfamiliar individual.

This invention also provides a method for manufacturing a reference electrode comprising the steps of: forming an electrode on an insulating substrate; and applying a liquid containing a polymer in which a pendant group having at least a fluoroalkylene block is attached to a non-fluorinated vinyl polymer, to the electrode directly or via another layer and then drying it to form a protection layer.

In this manufacturing process, a protection layer is formed by applying and then drying a liquid comprising a polymer having the above particular structure. Thus, there may be provided, with a good controllability for a film thickness, a protection layer which is excellent in stability for repeated measurement, adhesiveness to adjacent layers and durability. Since the liquid containing the above polymer has a lower viscosity, the protection layer may be readily formed with a reduced film thickness. Specifically, a protection layer 0.01 to 3 µm of thickness after drying may be satisfactorily formed.

DETAILED DESCRIPTION OF THE PREFERRED EMBODIMENTS

Figure 1:
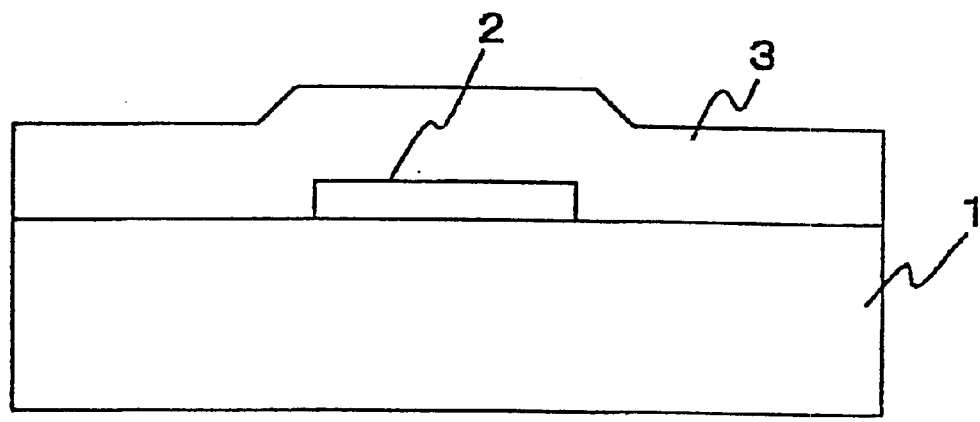
FIG. 1 is a cross section of an embodiment of a reference electrode according to this invention.

A "reference electrode" herein refers to an electrode as a standard for determining an electrode potential of a working electrode as described above. A "biosensor" herein comprises the above reference electrode and usually may further comprise a working electrode and/or a counter electrode. As used herein, a "measuring apparatus" refers to a system comprising the above biosensor and equipped with a variety of means for indicating and processing an electric signal from the biosensor. A reference electrode, a biosensor and a measuring apparatus according to this invention will be described in detail.

The first embodiment of a reference electrode according to this invention comprises an electrode on an insulating substrate and a protecting layer which covers the electrode and mainly consists of a polymer in which a pendant group containing at least a fluoroalkylene block is attached to a non-fluorinated vinyl polymer. The term "mainly consist (ing) of" as used herein means that the above polymer is a main component composing of the protection layer; for example, the polymer is contained in a proportion of 50 wt % or higher in the protection layer.

A "non-fluorinated vinyl polymer" is a moiety for improving adhesiveness to an electrode or a layer such as an organic polymer layer formed on the electrode. There are no limitations in terms of its structure, but it must have no fluorine atoms. If a polymer part other than a pendant group contains a fluorine atom, a protection layer may be less adhesive to an electrode or a layer such as an organic polymer layer formed on the electrode, making it difficult to prepare a solution and thus to form a protection layer as a thin film.

A non-fluorinated vinyl polymer is a polymer having a principal chain composed of carbon-carbon chain; preferably a homopolymer or copolymer of one or more monomers selected from the group consisting of unsaturated hydrocarbons, unsaturated carboxylic acids and unsaturated alcohols; most preferably a polycarboxylic acid. An appropriate polymer may be selected for improving adhesiveness to an electrode or a layer such as an organic polymer layer formed on the electrode to provide a protection layer having good durability. It is preferable that a fluoroalkylene block is attached to a vinyl polymer via an ester group, which is appropriately polar to further improve adhesiveness to an electrode or a layer such as an organic polymer layer formed on the electrode.

A pendant group containing a fluoroalkylene block is one having a fluoroalkylene group as a unit. A fluoroalkylene group means an alkylene group whose hydrogens are partially or totally replaced with fluorines. A fluorine content in the pendant group, i.e., a value of $x/(x+y)$ where x and y are the numbers of fluorine and hydrogen atoms in the pendant group, respectively, is preferably 0.3 to 1, more preferably 0.8 to 1, which may effectively prevent adhesion of contaminants to the protection layer.

The pendant group preferably has 3 to 15 carbon atoms, more preferably 5 to 10 carbon atoms, most preferably 8 to 10 carbon atoms, to make the length of the pendant group appropriate for providing good film-deposition property; effectively preventing adhesion of contaminants; and maintaining good adhesiveness to an adjacent electrode or polymer layer.

The binding rate of the pendant group to the vinyl polymer, i.e., the content of the pendant group, is not particularly limited, but may be appropriately determined depending on the other polymers and its application; for example, 0.1 to 30%. The content of the water-repellent pendant group may be thus selected in an appropriate range to realize good protection property for the electrode surface and good adhesiveness to an adjacent polymer layer. The binding rate of the pendant group means the proportion of the pendant group to all the groups attached to the carbon-carbon chain as the principal chain of the vinyl polymer. For example, where a vinyl polymer as a principal chain is polyacrylate, 10% of whose —COOH groups are esterified to be a pendant group, the binding rate of the pendant group is 2.5% obtained by multiplying the binding rate of —COOH group, 25%, by the esterification rate, 10%.

The second embodiment of a reference electrode according to this invention comprises an electrode on an insulating substrate and a protection layer which covers the electrode and mainly consists of a polycarboxylic acid (A) fluoroalcohol ester. The term "mainly consist(ing) of" herein means that the above polymer is a main component composing of the protection layer; for example, the polymer is contained in a proportion of 50 wt % or higher in the protection layer.

The third embodiment of a reference electrode according to this invention comprises an electrode on an insulating substrate and a protection layer which covers the electrode and comprises a polycarboxylic acid (A) fluoroalcohol ester and a polycarboxylic acid (B) alkylalcohol ester.

The fourth embodiment of a reference electrode according to this invention comprises an electrode on an insulating substrate and a protection layer which covers the electrode and mainly consists of a polycarboxylate comprising alkylalcohol ester and fluoroalcohol ester groups. The term "mainly consist(ing) of" herein means that the above polymer is a main component composing of the protection layer; for example, the polymer is contained in a proportion of 50 wt % or higher in the protection layer.

Examples of the polycarboxylic acid composing of the polycarboxylic acid (A) or (B) or the above polycarboxylate include polymers having a carboxylic acid unit such as acrylic acid, methacrylic acid, fumaric acid and itaconic acid; specifically polymethacrylic acid, polyacrylic acid and a copolymer of acrylic acid and methacrylic acid. The polycarboxylic acids (A) and (B) may be the same or different.

A polycarboxylic acid is a polymer having a carboxylic acid unit such as acrylic acid, methacrylic acid, fumaric acid and itaconic acid; for example polymethacrylic acid and polyacrylic acid.

A fluorine content in the fluoroalcohol ester group, i.e., a value of $x/(x+y)$ where x and y are the numbers of fluorine and hydrogen atoms in the fluoroalcohol ester group, respectively, is preferably 0.3 to 1, more preferably 0.8 to 1, which may prevent adhesion of contaminants to the protection layer.

The fluoroalcohol moiety composing of the fluoroalcohol ester group preferably has 3 to 15 carbon atoms, more preferably 5 to 10 carbon atoms, most preferably 8 to 10 carbon atoms, to make the length of the fluoroalcohol ester group appropriate for providing good film-deposition property; effectively preventing adhesion of, e.g., contaminants and maintaining good adhesiveness to an adjacent electrode or polymer layer.

The esterification rate of the polycarboxylic acid fluoroalcohol ester is not particularly limited, but may be appropriately determined depending on the other polymers and its application; for example, 0.1 to 30%. A esterification rate herein means the rate of the esterified carboxylic acid groups belonging to the polyacrylic acid moiety in the principal chain. The esterification rate may be selected within the above range to make the content of the water-repelling fluoroalcohol ester group proper for effectively preventing adhesion of contaminants to the protection layer and maintaining adhesiveness to an electrode or an organic polymer layer.

In this invention, the fluoroalcohol composing of the fluoroalcohol ester is preferably a primary alcohol because it may effectively prevent adhesion of contaminants to the protection layer and may provide excellent chemical resistance to acids, alkalis or a variety of organic solvents. Preferable examples of the alcohol include 1H, 1H-perfluorooctyl polymethacrylate and 1H, 1H,2H,2H-perfluorodecyl polyacrylate.

The protection layer may comprise a polycarboxylic acid (A) fluoroalcohol ester and a polycarboxylic acid (B) alkylalcohol ester or may mainly consist of a polycarboxylate comprising an alkylalcohol ester and a fluoroalcohol ester groups, to provide a reference electrode exhibiting improved high-temperature stability.

A preferable type of "fluoroalcohol ester" is as described above.

The alkylalcohol moiety in the alkylalcohol ester part means a straight or circular alcohol represented by $C_nH_{n+2}OH$ (n is a natural number) where n is an integer of 1 or more, preferably 2 to 10, more preferably 4 to 8, most preferably 6. For example, hexyl and cyclohexyl groups may be suitable. Thus, stability of the reference electrode may be further improved when exposed to an elevated temperature.

When the protection layer comprises a polycarboxylic acid (A) fluoroalcohol ester and a polycarboxylic acid (B) alkylalcohol ester, the content of the polylcarboxylic acid (A) fluoroalcohol ester to the overall protection layer is preferably 50 to 90 wt %, more preferably 75 to 99 wt %, most preferably 80 to 95 wt %. If the content is too low, the protection layer may be less durable while if the content is too high, the protection layer may exhibit insufficient stability when exposed to an elevated temperature. On the other hand, the content of the polylcarboxylic acid (B) alkylalcohol ester to the overall protection layer is preferably 1 to 50 wt %, more preferably 1 to 25 wt %, most preferably 5 to 20 wt %. If the content is too low, the protection layer may exhibit insufficient stability when exposed to an elevated temperature, while if the content is too high, the protection layer may be less durable. A polycarboxylic acid (B) alkylalcohol ester means a polycarboxylic acid (B) which is at least partially esterified with the above alkylalcohol; preferably cyclohexyl polymethacrylate.

When the protection layer comprises a polycarboxylate comprising an alkylalcohol ester and a fluoroalcohol ester groups, preferable types of individual ester groups are as described above and a variety of combination of these ester groups may be employed. The ratio between the alkylalcohol ester and the fluoroalcohol ester groups is not particularly limited, but a/b where "a" and "b" are the numbers of the fluoroalcohol ester group and of the alkylalcohol ester group, respectively, is preferably 50150 to 99/1, more preferably 75/25 to 99/1, most preferably 80/20 to 95/5.

Preferable polycarboxylates include those containing the repeating unit represented by formula (1). When the COO—R group is cyclohexyl polymethacrylate, it may improve high-temperature stability and electrode-protecting property;

FORMULA 1

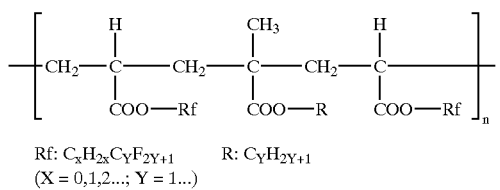

Rf: $C_xH_{2x}C_yF_{2Y+1}$   R: $C_YH_{2Y+1}$
(X = 0,1,2...; Y = 1...)

where n is an integer of 2 or more, X is an integer of 0 or more, and Y is an integer of 1 or more.

Specific compounds include a copolymer of 1H,1H-perfluorooctyl methacrylate and cyclohexyl methacrylate and a copolymer of 1H,1H,2H,2H-perfluorodecyl acrylate and cyclohexyl methacrylate; preferably a compound represented by formula (2) having the repeating units of 1H,1H, 2H,2H-perfluorodecyl acrylate and of cyclohexyl methacrylate.

FORMULA 2

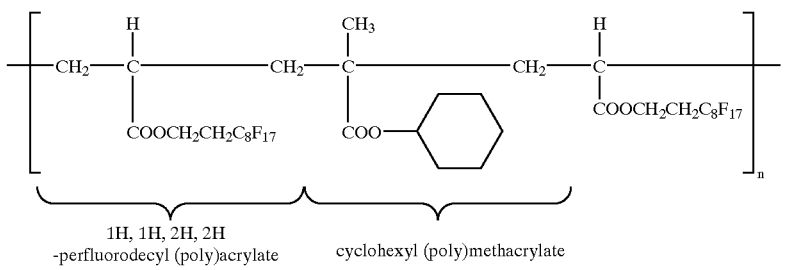

1H, 1H, 2H, 2H -perfluorodecyl (poly)acrylate   cyclohexyl (poly)methacrylate where n is an integer of 2 or more.

These copolymers may be used to improve particularly high-temperature stability and other properties such as electrode-protecting property.

As described above, a protection layer in a reference electrode according to this invention comprises a particular structure of polymer, but may comprises a mixture of two or more polymers whose structures and/or molecular weights are different from each other.

In these reference electrodes, the thickness of the protection layer is preferably 0.0.01 to 3 μm, more preferably 0.01 to 1 μm, most preferably 0.01 to 0.1 μm, which may lead to improvement in sensitivity and responsiveness and reduction in a washing time.

In this invention, the molecular weight of the polymer composing the protection layer is preferably 1000 to 50000, more preferably 3000 to 30000. A molecular weight as used herein refers to a number average molecular weight, which is determined by GPC (Gel Permeation Chromatography). If the molecular weight is too high, it is difficult to prepare a solution, leading to form a thin protection layer while if it is too low, adhesion of contaminants may not be adequately prevented. When the protection layer comprises the polycarboxylic acid (A) fluoroalcohol ester and the polycarboxylic acid (B) alkylalcohol ester, it is desirable that any of these polymers has a molecular weight within the above range.

As described above, a reference electrode according to this invention comprises a protection layer comprising a fluorine-containing polymer, which is characterized by having the above particular structure, so that the protection layer may prevent adhesion of contaminants to the reference electrode and improve stability in a measuring sensitivity during a long-term use. It is also well-known as an application of a fluorine-containing polymer in a biosensor that a NAFION® film, an ion-exchange polymer, is disposed on an immobilized enzyme layer of a working electrode (JP-A 8-50112), but a polymer having such a structure does not realize the effects given by this invention. NAFION® is a cation-exchange polymer in which perfluoroalkylene ether side chains having a terminal sulfonic group are attached to a perfluoromethylene principal chain (Formula 3).

FORMULA 3

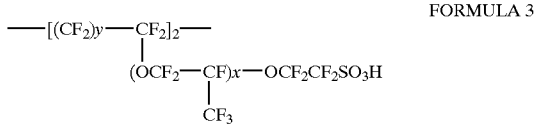

A NAFION® film is, however, used for preventing permeation of ionic interferent materials interfering with an electrode reaction, and thus may little protect a reference electrode.

A working electrode in a biosensor according to this invention is desirably an enzyme electrode. An enzyme electrode refers to an electrode comprising an immobilized enzyme layer on an electrode surface. An immobilized enzyme layer comprises an organic polymer base material in which a catalytic enzyme is immobilized. The immobilized enzyme layer may be formed by, for example, adding dropwise and applying by spin-coating a solution containing some kind of enzyme, a protein cross-linking agent such as glutaraldehyde and albumin. Albumin may protect the enzyme from a reaction with the cross-linking agent and may be a protein base material. Enzymes to be immobilized include lactate oxidase, glucose oxidase, urate oxidase, galactose oxidase, lactose oxidase, sucrose oxidase, ethanol oxidase, methanol oxidase, starch oxidase, amino acid oxidase, monoamine oxidase, cholesterol oxidase, choline oxidase and pyruvate oxidase, which generate hydrogen peroxide as a product of their catalytic reaction or consume oxygen.

Two or more enzymes may be used in combination for generating hydrogen peroxide; for example any combination of creatininase, creatinase and sarcosine oxidase for allowing creatinine to be detected.

An enzyme may be combined with a coenzyme; for example, a combination of 3-hydroxybutyrate dehydrogenase and nicotinamide adenine dinucleotide (NAD) for allowing 3-hydroxybutyric acid to be detected. An enzyme may be combined with an electron mediator, where an electron mediator which has been reduced by the enzyme is oxidized on the electrode surface to generate an oxidation current which is then measured. A specific combination is glucose oxidase and potassium ferricyanide. Such a combination may allow glucose to be detected.

As described above, there are no limitations to the structure of the immobilized enzyme layer as long as it contains at least an enzyme and can convert a target substance into an electrode sensitive substance such as hydrogen peroxide.

Figure 5:
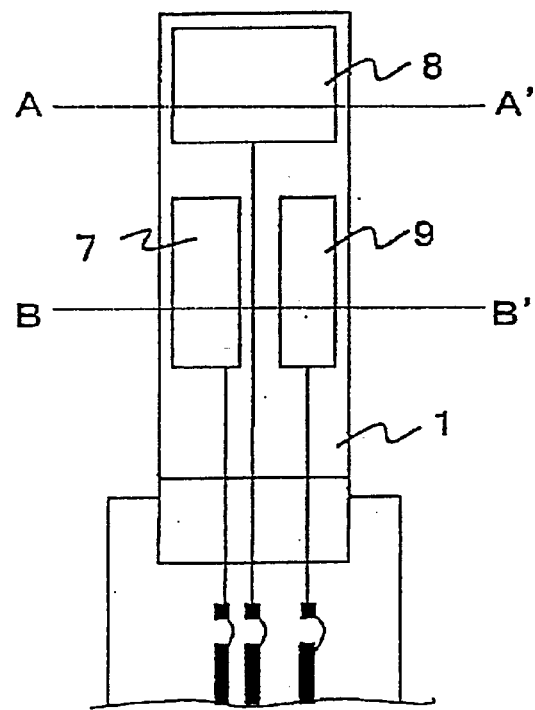
FIG. 5 schematically shows the structure of a biosensor (urinary-sugar sensor) according to this invention.
Figure 5:
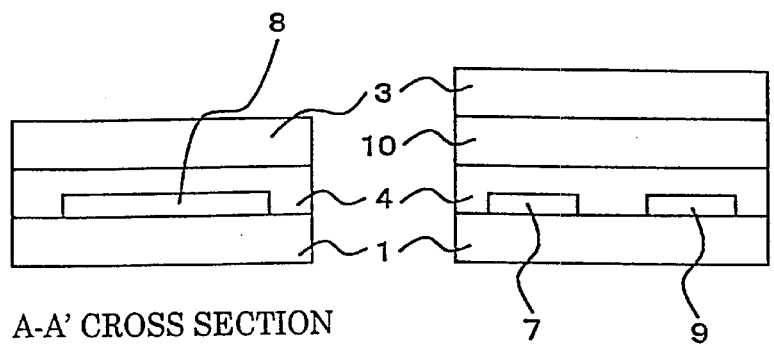

FIG. 5 shows an example of a biosensor employing a reference electrode of this invention, where a working electrode 7, a counter electrode 8 and a reference electrode 9 are formed on a quartz substrate. The working electrode 7 and the counter electrode 8 are platinum electrodes, and the reference electrode 9 is a silver/silver chloride electrode. On the counter electrode 8 are sequentially formed a binding layer 4 and a protection layer 3. On the working electrode 7 and the reference 9 are sequentially formed a binding layer 4, an immobilized enzyme layer 10 and a protection layer 3. The binding layer 4 mainly consists of γ-aminopropyltriethoxysilane. There are no limitations for the structure of the immobilized enzyme layer 10 as long as it contains at least an enzyme and can convert a target substance into an electrode sensitive substance such as hydrogen peroxide. The protection layer 3 mainly consists of a methacrylate-resin fluoroalcohol ester. The working electrode 7, the counter electrode 8 and the reference electrode 9 are connected to corresponding measuring systems, respectively. Such a structure may contribute to extending the life of the biosensor and stabilizing its properties. This figure shows an example of an amperometric type of sensor, but the reference electrode of this invention may be, of course, applied to an ion-sensitive field effect transistor type of sensor.

In a measuring apparatus according to this invention, a biosensor is preferably removable because it is desirable that the electrode of the biosensor is readily exchangeable since the electrode is consumable. Only the biosensor may be removable or wirings connecting the biosensor to other parts or a part comprising the biosensor may be removable. For example, in the measuring apparatus shown in FIG. 6, a wiring 54 between a biosensor 50 and an electrochemical measuring circuit 51 may be removable, or a part consisting of the biosensor 50, the wiring 54 and the electrochemical measuring circuit 51 may be removable.

A data processor in a measuring apparatus according to this invention calculates a determination value based on an electric signal from a biosensor; for example, it operates by converting the electric signal to an analogue signal and/or a digital signal for calculating a determination value. The data processor may be equipped with a variety of means; for example, some or all of the following means;

(a) a timer;

(b) a time setting means for setting a time and a time indicator indicating a time at the time set by the time setting means;

(c) an operation guide means describing operation instructions for the measuring apparatus;

(d) a measured-value storing means for storing a calculated measured value;

(e) a password registration means for registering a password for a user of the measuring apparatus;

(f) a memo registration means for registering a memo;

(g) an operation indicator for detecting malfunction in the measuring apparatus;

(h) a calibration-timing indicator for detecting and indicating a calibration timing for the biosensor;

(i) an electrode-replacement-timing indicator for detecting and indicating a replacement timing for the electrode in the biosensor;

(j) an abnormal-current indicator for detecting and indicating an abnormal current; and (k) a calibrator for calibrating the biosensor.

Such a configuration may further improve operability. Processed results from one or more of (a) to (k) are indicated by the indicator.

A method for manufacturing a reference electrode according to this invention comprises the steps of: forming an electrode on an insulating substrate; and applying a liquid containing a polymer in which a pendant group having at least a fluoroalkylene block is attached to a non-fluorinated vinyl polymer, to the electrode directly or via another layer and then drying it to form a protection layer. A preferred embodiment for "a polymer in which a pendant group having at least a fluoroalkylene block is attached to a non-fluorinated vinyl polymer" is as described for the above first to fourth reference electrodes according to this invention; for example, fluoroalcohol polycarboxylates such as 1H,1H-perfluorooctyl polymethacrylate, 1H, 1H,2H,2H-perfluorodecyl polyacrylate, a copolymer of 1H,1H-perfluorooctyl methacrylate and cyclohexyl methacrylate, and a copolymer of 1H,1H,2H,2H-perfluorodecyl acrylate and cyclohexyl methacrylate.

Embodiments of this invention will be further described with reference to the drawings.

Embodiment 1

The first embodiment will be described with reference to FIG. 1. The reference electrode of this embodiment comprises an electrode 2 as a reference electrode on an insulating substrate 1, on which a binding layer 3 consisting of methacrylate-resin polyfluoroalcohol ester is formed.

The insulating substrate 1 may mainly consisting of a highly-insulative material such as ceramics, glass, quartz and plastics, which is preferably excellent in waterproof, heat resistance, chemical resistance and adhesiveness to an electrode.

The electrode is desirably a silver/silver chloride electrode, which may be easily formed on the insulating substrate 1 and may be easily handled. The structure of the silver/silver chloride electrode is preferably a laminated film in which either titanium, silver and silver chloride or titanium, platinum, silver and silver chloride are sequentially deposited because of its improved sensitivity and strength. The electrode 2 may be formed by, for example, spattering, ion plating, vacuum deposition, chemical paper deposition and electrolysis. For example, a silver/silver chloride electrode may be manufactured by forming a silver film by spattering, then immersing the substrate in an aqueous solution containing a chloride compound whose ionization tendency is higher than silver, e.g., an aqueous solution of ferric chloride, and then conducting electrolysis for the system.

A methacrylate-resin fluoroalcohol ester composing of the protection layer 3 is a methacrylate-resin whose carboxyl groups are partially or totally esterified by a fluoroalcohol. The fluoroalcohol is an alcohol, one or more or all of whose hydrogens are replaced with fluorine atoms. For example, 1H,1H-perfluorooctyl polymethacrylate or 1H,1H,2H,2H-perfluorodecyl polyacrylate may be used. In this invention, for example, 1H,1H-perfluorooctyl polymethacrylate is a polymer in which methacrylic acid moieties are partially or totally esterified by 1H,1H-perfluorooctylalcohol.

The protection layer 3 may be formed by adding dropwise and applying by spin-coating a solution of a methacrylate-resin fluoroalcohol ester in a perfluorocarbon solvent such as perfluorohexane on the immobilized enzyme layer 4 in which a catalytic enzyme is immobilized. The concentration of the methacrylate-resin fluoroalcohol ester in the solution may be preferably 0.1 to 5 wt %, more preferably about 0.3 wt %, depending on a target substance because a concentration within the range may provide good film-deposition property and may effectively prevent adhesion of contaminants.

There are no limitations to a process for forming the protection layer 3 as long as a uniform layer may be formed; spray coating or dip-coating may be, in addition to spin-coating, employed.

Embodiment 2

Figure 2:
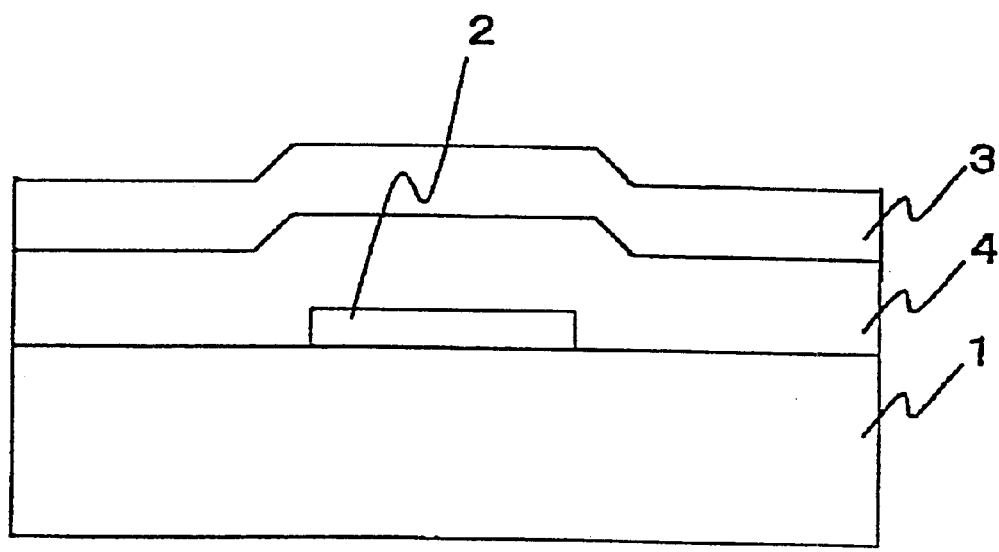
FIG. 2 is a cross section of another embodiment of a reference electrode according to this invention.

This embodiment will be described with reference to FIG. 2. The reference electrode of this embodiment comprises an electrode 2 as a reference electrode on an insulating substrate 1, on which a binding layer 4 consisting of γ-aminopropyltriethoxysilane and a protection layer 3 consisting of methacrylate-resin polyfluoroalcohol ester are sequentially formed. The reference electrode is characterized by having the binding layer 4 mainly consisting of a silane-coupling agent between the electrode 2 and the protection layer 3.

The protection layer 3 may be formed as described in Embodiment 1.

The binding layer 4 is formed to improve a binding strength between the electrode 2 and the protection layer 3, as well as to modify the surfaces of the insulating substrate 1 and the electrode 2 into hydrophilic surfaces for improving uniformity in the film thickness of the protection layer 3.

The binding layer 4 mainly consists of a silane-coupling agent. Silane-coupling agents which may be used include aminosilanes, vinylsilanes and epoxysilanes. γ-aminopropyltriethoxysilane, an aminosilane, is particularly preferable in the light of adhesiveness. The binding layer 4 may be formed by, for example, applying a silane-coupling agent solution by spin-coating, where the concentration of the silane-coupling agent is preferably about 1 v/v% (volume %) for achieving good adhesiveness.

Embodiment 3

This embodiment will be described with reference to FIG. 1. The reference electrode of this embodiment comprises an electrode 2 as a reference electrode on an insulating substrate 1, on which a protection layer 3 mainly consisting of acrylate-resin polyfluoroalcohol ester and cyclohexyl polymethacrylate is formed. A binding layer mainly consisting of a silane-coupling agent may be formed between the protection layer 3 and the electrode 2.

A acrylate-resin polyfluoroalcohol ester may be, for example, 1H,1H,2H,2H-perfluorodecyl polyacrylate.

The protection layer 3 may be formed, for example, by adding dropwise and applying by spin-coating a mixed solution of 1H,1H,2H,2H-perfluorodecyl polyacrylate and cyclohexyl polymethacrylate in xylene hexafluoride on the electrode 2. The concentration of 1H,1H,2H,2H-perfluorodecyl polyacrylate in the mixed solution may be preferably 0.1 to 5 wt %, more preferably about 1 wt %, depending on a target substance. The concentration of cyclohexyl polymethacrylate may be preferably up to 10 wt %, more preferably about 1 wt %, depending on a target substance. Cyclohexyl polymethacrylate within the above concentration range may be added to 1H,1H,2H,2H-perfluorodecyl polyacrylate to improve physico-chemical properties of the protection layer; in particular its resistance to shock, scratch and distortion.

Embodiment 4

This embodiment is an example of a process for manufacturing a reference electrode according to this invention.

First, an electrode consisting of silver/silver chloride is formed on a substrate of quartz.

Then, the surfaces of the electrode and of the substrate are washed. The process may be conducted with, for example, an organic solvent or acid, an ultrasonic cleaner or combination thereof. A solvent or acid used should not cause damage to the electrode materials. The organic solvent is preferably a polar solvent; for example, ketones such as acetone and alcohols such as isopropyl alcohol. The acid is, for example, diluted sulfuric acid. Electrolysis cathode water, which is a solution generated around a cathode during electrolysis of pure water, may be used. Electrolysis cathode water is neutral to weakly alkaline and highly reductive, so that it can minimize damage to the substrate and the electrodes while making the potentials on the surfaces of the substrate and of adhered particles negative, to prevent detached particles from re-adhesion. Among the above procedures, a process of sequentially washing with acetone and sulfuric acid is preferable.

Then, a binding layer is formed on the electrode surface. As described above, the binding layer may be preferably made of a silane-coupling agent such as γ-aminopropyltriethoxysilane.

A coupling agent may be applied by, for example, spin-coating, spray-coating, dip-coating and a hot stream method. Spin-coating is a process that a solution or suspension of components for a binding layer such as a coupling agent is applied with a spin coater, by which a thinner binding layer may be formed, adequately controlling its thickness. Spray-coating is a process that for example, a solution of a coupling agent is sprayed on a substrate and dip-coating is a process that a substrate is soaked into, for example, a solution of a coupling agent. By these process, a binding layer may be formed by simple steps without no special apparatuses. A hot stream method is a process that for example, a stream of a coupling agent solution is flown over a substrate at an elevated temperature, by which a thinner binding layer may be formed, adequately controlling its thickness.

After applying the coupling agent solution, the substrate is dried generally, but not limited to, at an ambient temperature to 170° C., for 0.5 to 24 hours depending on the temperature. Drying may be conducted in the air or in an inert gas such as nitrogen; for example, a nitrogen blowing may be employed, in which nitrogen is blown on the substrate to be dried.

After forming the binding layer, on the substrate is applied, for example, a solution of a polycarboxylic acid fluoroalcohol ester to form a protection layer, by, for example, spin-coating, dip-coating, spray-coating or brush coating, preferably spin-coating because of its thickness controllability. By spin-coating, a protection layer as a film about 0.01 to 3 μm of thickness may be formed, adequately controlling its thickness. Alternatively, the substrate is soaked into the above solution by dipping for application thereof, and is then dried by nitrogen blowing, by which a protection layer may be formed by a simple process.

After applying the solution, the substrate is dried at a temperature which does not impair enzyme activity, preferably an ambient temperature (25° C.) to 40° C., for 0.5 to 24 hours depending on the drying temperature. Drying may be conducted in the air or in an inert gas such as nitrogen; for example, a nitrogen blowing may be employed, in which nitrogen is blown on the substrate to be dried.

As described above, a reference electrode may be manufactured, in which different layers with particular functions are formed on an electrode.

Embodiment 5

Figure 12:
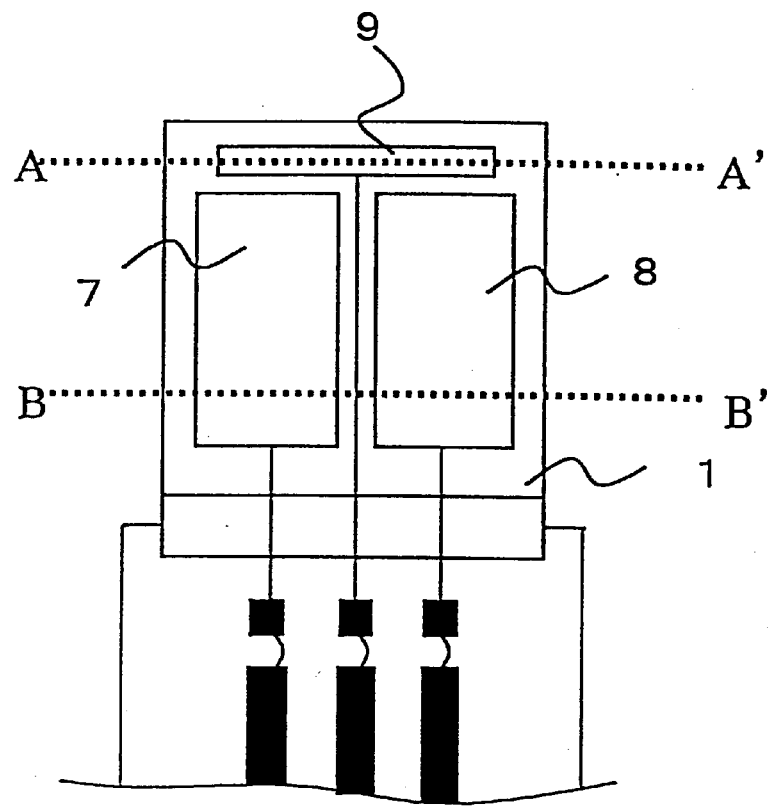
FIG. 12 shows a configuration example of a biosensor according to this invention.
Figure 12:
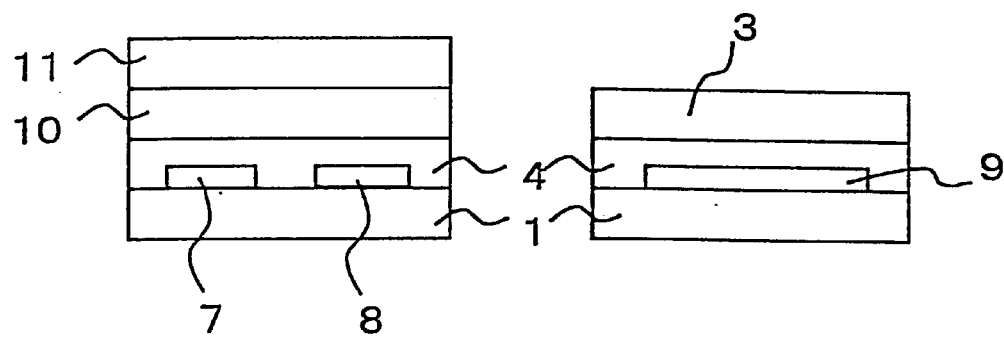

FIG. 12 shows an example of a biosensor according to this invention, where a working electrode 7, a counter electrode 8 and a reference electrode 9 are formed on the same insulating substrate 1. On the working electrode 7 and the counter electrode 8, there are formed a binding layer 4, an immobilized enzyme layer 10 and a permeation restricting layer 11 in sequence. On the reference electrode 9, there are formed a binding layer 4 and a protection layer 3 in sequence.

Figure 13:
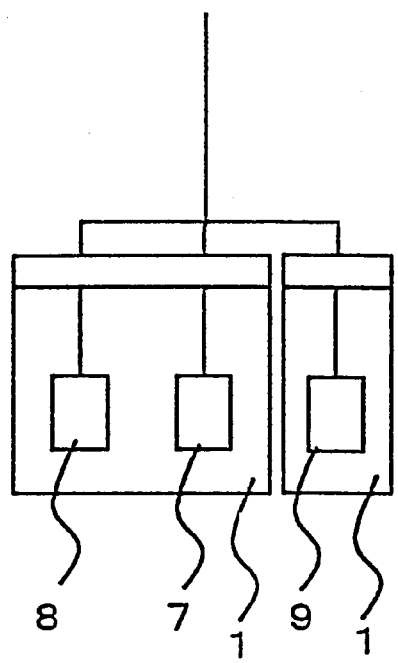
FIG. 13 shows a configuration example of a biosensor according to this invention.
Figure 13:
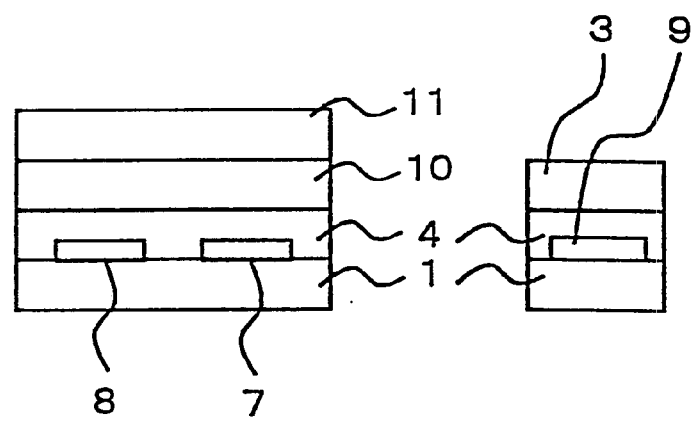

FIG. 13 shows another example of a biosensor according to this invention, where a working electrode 7 and a counter electrode 8 are formed on the same insulating substrate 1 while a reference electrode 9 is formed on another insulating substrate 1. On the working electrode 7 and the counter electrode 8, there are formed a binding layer 4, an immobilized enzyme layer 10 and a permeation restricting layer 11 in sequence. On the reference electrode 9, there are formed a binding layer 4 and a protection layer 3 in sequence.

Figure 14:
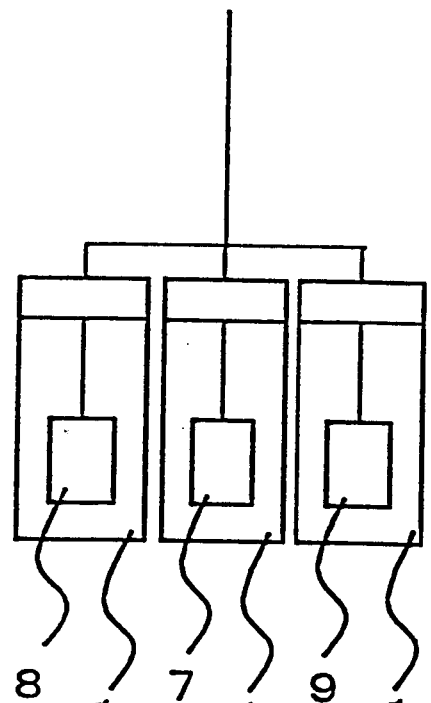
FIG. 14 shows a configuration example of a biosensor according to this invention.
Figure 14:
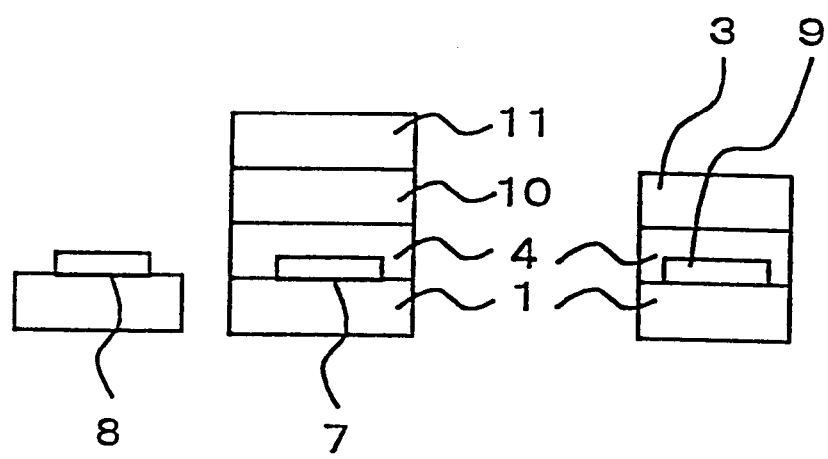

FIG. 14 shows another example of a biosensor according to this invention, where a working electrode 7, a counter electrode 8 and a reference electrode 9 are formed on different insulating substrates 1, respectively. On the working electrode 7 and the counter electrode 8, there are formed a binding layer 4, an immobilized enzyme layer 10 and a permeation restricting layer 11 in sequence. On the reference electrode 9, there are formed a binding layer 4 and a protection layer 3 in sequence.

As described above, a working electrode 7, a counter electrode 8 and a reference electrode 9 may be formed on the same substrate or different substrates.

Embodiment 6

This embodiment is an example of a measuring apparatus according to this invention equipped with a biosensor, an electrochemical measuring circuit, a data processor and a data indicator, which will be described with reference to FIGS. 6 and 7.

Figure 6:
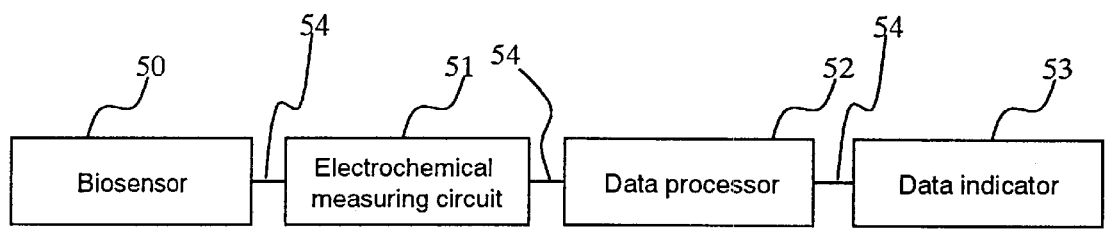
FIG. 6 shows a configuration example of a measuring apparatus according to this invention.

The measuring apparatus, as shown in FIG. 6, comprises a biosensor 50, an electrochemical measuring circuit 51, a data processor 52 and a data indicator 53, which are connected by wirings 54.

The biosensor 50 may comprises a reference electrode, for example, described in any of Embodiments 1 to 4. Since the biosensor 50 is consumable, it is preferably removable for facilitating replacement.

The electrochemical measuring circuit 51 is a potentiostat in this embodiment, but it may be any circuit which may apply a constant potential to the biosensor 50 to determine a current value.

Figure 7:
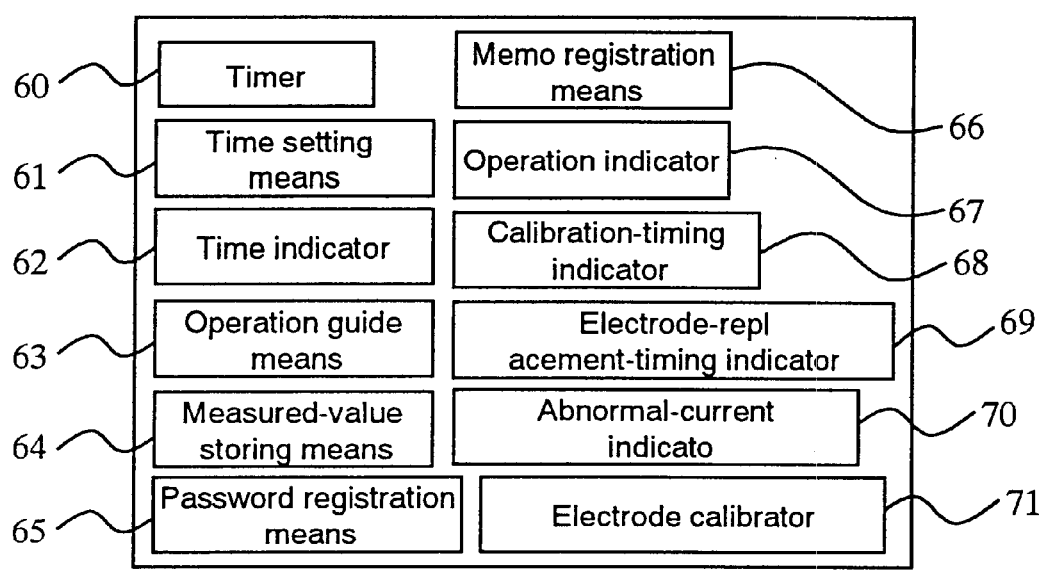
FIG. 7 shows a configuration example of a data processor in a measuring apparatus according to this invention.

The data processor 52 has a configuration shown in FIG. 7, comprising a timer 60, a time setting means 61, a time indicator 62, an operation guide means 63, a measured-value storing means 64, a password registration means 65, a memo registration means 66, an operation indicator 67, a calibration-timing indicator 68, an electrode-replacement-timing indicator 69, an abnormal-current indicator 70 and a calibrator 71. The processor comprising these means may allow an operator to smoothly conduct calibration of the electrode, measurement and storage of measurement data. Although this embodiment has a personal computer (hereinafter, referred to as a "PC") as a data processor 52, it may be any apparatus having an operation unit such as a microprocessor which may process a signal from the electrochemical circuit 51. A signal processed by the data processor 52 is converted into a measured value, which is then indicated by the data indicator 53.

In this embodiment, the data indicator 53 is a display for PC, but it may be any apparatus which may indicate data processed by the data processor 52. The data processed by the data processor 52 may include a measured value calculated by the data processor 52, status (normal or malfunction) of the biosensor 50, detection results for an abnormal current value, a timing for replacing the biosensor 50, a timing and a procedure for calibration of the biosensor 50, a date, a time, a clock, a signal from the electrochemical measuring circuit 51 which is processed by the operation unit in the data processor 52, instructions for operation means for initial setting, and instructions giving an advice during operation. An indicating means may be a digital number, an analogue number or voice. Other indicating means may include beep, light, vibration, color, graphic and heat, but a digital or analogue number is preferable.

The wiring 54 may be any electric wire which can connect these.

Next, each means in the data processor 52 (FIG. 7) will be described.

The timer 60 is a clock built in a PC, but it may be any type giving a time to the operation unit.

The time setting means 61 sets a time when a measurement is performed, using the timer 60. In this embodiment, the means utilizes some functions of the clock built in the PC as is for the timer 60, but it may be any type which can give a time to the operation unit as well as set a time of measurement. It is preferable that a plurality of times can be set for facilitating multiple measurements a day. It may be more convenient that an operator can select whether using the time setting means 61 or not.

The time indicator 62 indicates a time set by the time setting means 61. For example, the time setting means 61 set to indicate a time every 12 hours allows an operator to know a measuring time every 12 hours from the time indicator 62.

The operation guide means 63 describes an operation procedure for a measuring apparatus or instructions for operation. Use of the operation guide means 63 can be selected by setting as appropriate.

The measured-value storing means 64 stores a measured value from the measuring apparatus or other information. Its semiconductor storage element is preferably a RAM (random access memory). The measured-value storing means 64 can preferably store a plurality of measured values. The measured-value storing means 64 can store not only a measured value, but also a variety of information to be processed by the data processor 52. Data to be stored can be controlled by setting as appropriate.

The password registration means 65 controls use of the measuring apparatus by an individual other than a particular operator and data on measured values for allowing user's privacy to be protected. A password is preferably constructed with a four or more digit number or alphanumeric for ensuring higher security. The password registration means 65 can preferably register a plurality of passwords for protecting two or more users' privacy. In this embodiment, any data cannot be input/output without a four digit password although use of the password registration means 65 can be appropriately selected by setting.

Preferably, the memo registration means 66 comprises a memo register for registering a memo, a memo itemizing means for accessing a registered memo group, a memo selector for selecting a memo item to be registered from the accessed memo group and a memo access means for accessing the memo selected by the memo selector. In this embodiment, the memo registration means having the configuration can register subject's data such as weight, blood pressure and temperature at measurement. Use of the memo registration means 66 can be appropriately selected by setting.

The operation indicator 67 indicates a status when one or both of the wirings 54 between the biosensor 50 and the electrochemical measuring circuit 51 and between the electrochemical measuring circuit 51 and the data processor 52 are disconnected. Use of the operation indicator 67 can be appropriately selected by setting.

The calibration-timing indicator 68 indicates a timing for calibration of the biosensor 50. After being used to a certain extent, a biosensor should be calibrated. Thus, the calibration timing indicator 68 indicates a calibration timing. The timing may be determined, based on an accumulated measuring time or the number of measurement. In this embodiment, one or both of the criteria can be selected as criteria for calibration, by setting.

The electrode-replacement-timing indicator 69 indicates timing for replacing an electrode in the biosensor 50. The timing may be determined, based on some criteria such as an accumulated measuring time, the number of measurement and voltage drop in a battery. In this embodiment, one or all of the factors can be selected as criteria for calibration, by setting.

The abnormal-current indicator 70 indicates a status when measurement cannot be conducted due to an abnormal current passing through the biosensor 50, the electrochemical measuring circuit 51, the data processor 52 and/or the wirings 54 connecting these or when some of these elements are broken.

"Indication" in the operation indicator 67, the calibration-timing indicator 68, the electrode-replacement-timing indicator 69 and the abnormal current indicator 70 may be, for example, performed through the above data indicator to inform certain data of a measuring apparatus operator.

The calibrator 71 is used during an initial stage of use or calibration. It can indicate a calibration procedure for the biosensor 50 and calibrate the biosensor 50. The calibration procedure may be indicated through the calibration-timing-indicator 68.

The measuring apparatus of this embodiment indicates various data such as the lifetime of a biosensor, a timing of calibration and an operation procedure for the device, so that even an unfamiliar individual can conduct precise measurement.

Although as shown in FIG. 6 this embodiment has a configuration where the biosensor 50, the electrochemical measuring circuit 51, the data processor 52 and the data indicator 53 are connected via the wirings 54, an alternative configuration may be employed, in which an electrochemical measuring circuit 51 and a data indicator 53 are directly connected without a data processor 52. In such a configuration, an analogue signal from the biosensor 50 is directly sent to the data indicator 53, which then indicates a measured value via, for example, an indicating system of a graduation and a pointer. It may be helpful to provide a table for converting an indicated value into an urinary-sugar or blood-sugar value.

Embodiment 7

This embodiment relates to a measuring apparatus as shown in FIG. 6 which is further equipped with a temperature sensor 56 and a pH sensor 57. It will be described with reference to FIG. 8.

Figure 8:
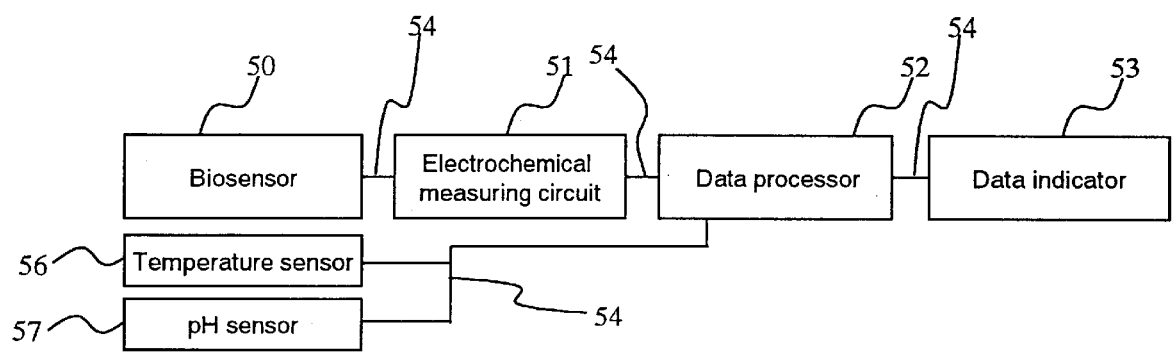
FIG. 8 shows a configuration example of a measuring apparatus according to this invention.

As shown in FIG. 8, the measuring apparatus comprises a biosensor 50, an electrochemical measuring circuit 51, a data processor 52, a data indicator 53, a temperature sensor 56 and a pH sensor 57, which are connected via wirings 54.

The data processor 52 processes an electric signal from the temperature sensor 56 and the pH sensor 57 to calculate the temperature and the pH. Then, a measured value for a particular component in a test sample estimated in the data processor 52 is corrected on the basis of the temperature and the pH to indicate the corrected data by the data indicator 53.

The temperature sensor 56 may be any type which can provide a form of data processor by the data processor 52, preferably a thermoelectric thermometer or resistance thermometer. The temperature sensor 56 measures a test-sample or ambient temperature. When measuring a sample temperature, the temperature sensor 56 is formed on the substrate comprising the biosensor having a reference electrode, for precisely determining the sample temperature and accurately correcting a measured value in detecting a particular component in the test sample. When the measuring apparatus has the biosensor and the temperature sensor separately, these sensors may be soaked in the test sample at the same time, for eliminating necessity for replacing the temperature sensor and the biosensor as one unit, leading to cost reduction. When measuring an ambient temperature, the temperature sensor 56 separately formed from the biosensor is placed in an ambient. The temperature sensor 56 is placed, for example, within the data indicator 53 or the electrochemical measuring circuit 51, for facilitating monitoring whether the ambient temperature is within measurable limits.

Figure 15:
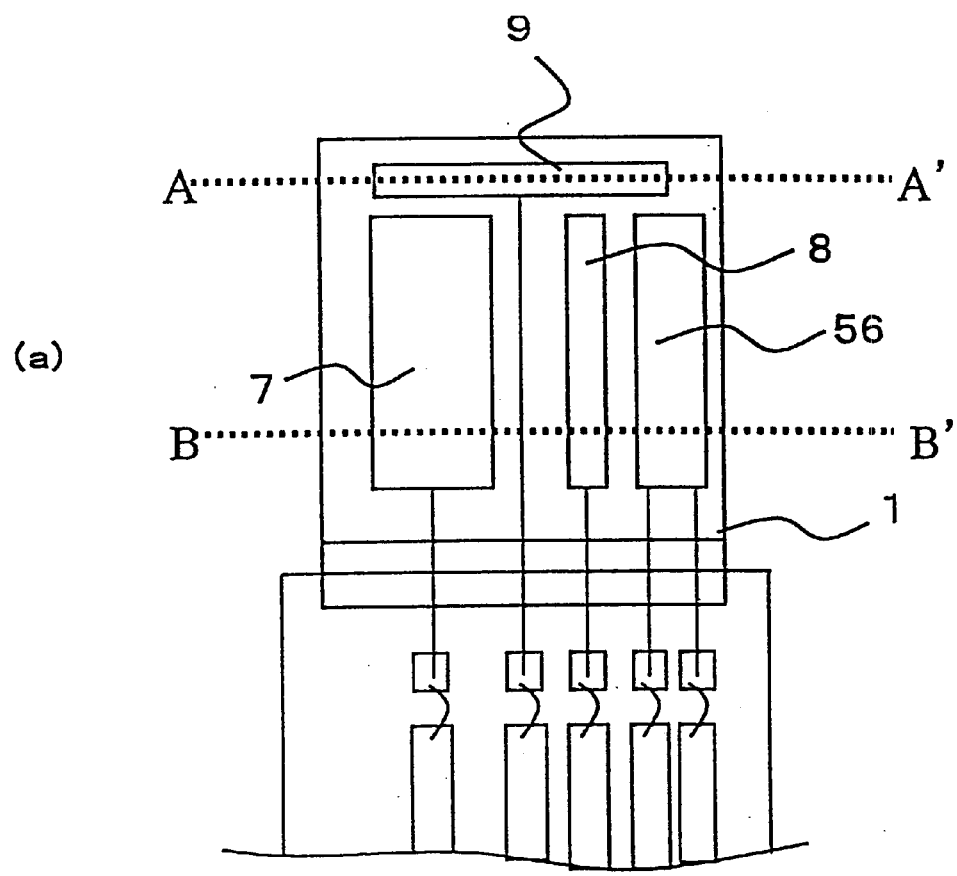
FIG. 15 shows a configuration example of a biosensor according to this invention.
Figure 15:
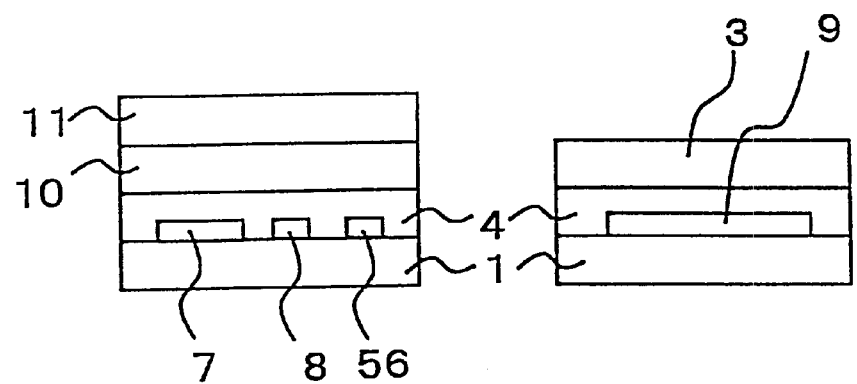

FIG. 15 shows an example of a measuring apparatus in which a temperature sensor 56 is formed on a substrate comprising a biosensor. The measuring apparatus comprises a working electrode 7, a counter electrode 8, a reference electrode 9 and also a temperature sensor 56. On the working electrode 7, the counter electrode 8 and the temperature sensor 56 are sequentially formed a binding layer 4, an immobilized enzyme layer 10 and a permeation restricting layer 11. On the reference electrode 9 are formed a binder layer 4 and a protection layer 3. Such a configuration may allow a measured value to be accurately corrected on the basis of a temperature.

The pH sensor 57 is preferably, but not limited to, a glass electrode or ion-sensitive field effect transistor. The pH sensor 57 may be calibrated using a solution of a pH indicator in a calibration liquid for configuring the biosensor 50, for allowing calibration of the biosensor 50 and the pH sensor 57 at the same time. The pH indicator may be preferably an oxalate or phthalate solution which is used in a common glass pH meter.

The measuring apparatus of this embodiment may permit to accurately determine a concentration of a particular component in a test sample in a wide temperature or pH range because a measured value from the biosensor can be corrected using a temperature and a pH for each test sample.

Although this embodiment has a configuration where the temperature sensor 56 and the pH sensor 57 are connected to the data processor 52, these may be connected to an electrochemical measuring circuit 51.

Embodiment 8

This embodiment relates to a measuring apparatus as shown in FIG. 8, further comprising a communication processor 58 connected to a data processor 52, which transmits data from the data processor to an external device. It will be described with reference to FIG. 9.

Figure 9:
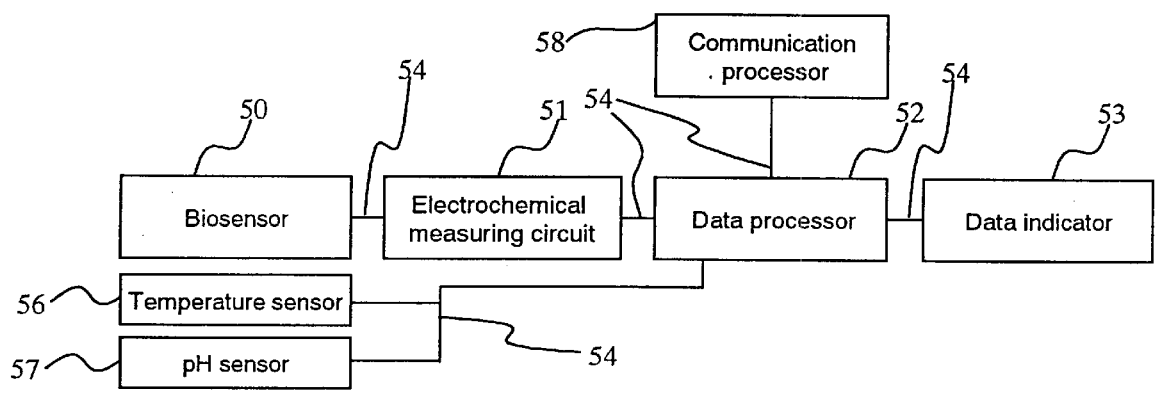
FIG. 9 shows another configuration example of a measuring apparatus according to this invention.

The measuring apparatus of this embodiment, as shown in FIG. 9, comprises a data processor 52 and a communication processor 58 which are mutually connected via a wiring 54. The communication processor 58 transmits information on a measured value to an external device. It is commonly a modem, but any device capable of communication processing may be used. A communication circuit used for communication may be, but not limited to, a telephone line, an infrared system or a wireless telephone. Information to be transmitted include those processed in the data processor 52 and those indicated by the data indicator 53. The communication processor 58 can transmit, for example, a current value in the biosensor 50, a password, a pH, a temperature, notes, a measured value calculated in the data processor 52, a timing for replacing the biosensor 50, a timing for calibration of the biosensor 50, data for checking operation or malfunction of the biosensor 50, an abnormal current and a signal from the electrochemical measuring circuit 51 processed by the operation unit of the data processor 52, to an external device such as a server or computer connected to the apparatus via a communication circuit. Information to be transmitted may be selected by setting as appropriate.

The measuring apparatus of this embodiment may be used to determine an urinary-sugar concentration in a patient with diabetes by him/herself at home, which may be then transmitted to a medical institute such as a hospital via a telephone line. It, therefore, may allow the patient to be appropriately advised in terms of diet or exercise control by the institute. Thus, it may allow administrating a patient with diabetes at home. Furthermore, since the apparatus can transmit data on malfunction of the biosensor, services such as repair or maintenance of the apparatus from its manufacturer as appropriate.

Embodiment 9

This embodiment relates to a measuring apparatus as shown in FIG. 9 further comprising a printer 59, which will be described with reference to FIG. 10.

Figure 10:
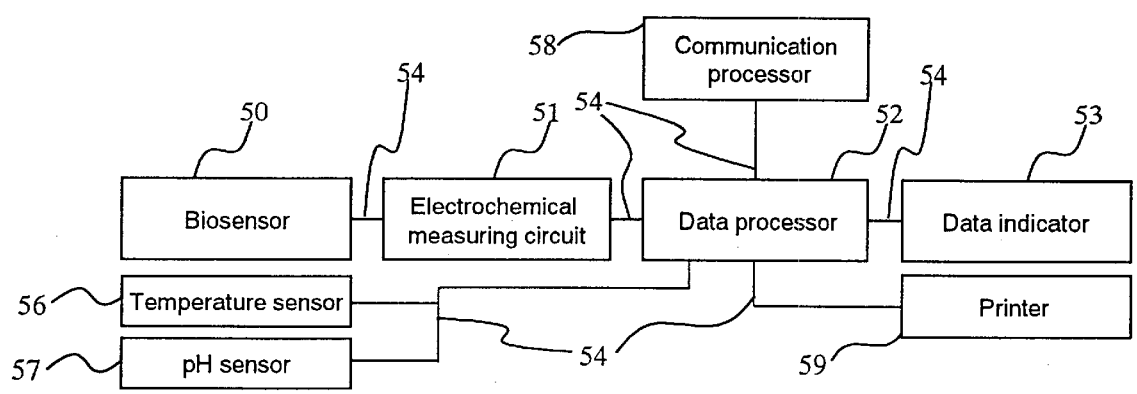
FIG. 10 shows another configuration example of a measuring apparatus according to this invention.

The measuring apparatus of this embodiment, as shown in FIG. 10, comprises a data processor 52 and a printer which are mutually connected via a wiring 54. The printer 59 may be, but not limited to, a thermal, heat transfer, dot impact, inkjet or laser-beam dry printer, preferably a thermal printer which is of low cost and simple. The wiring 54 connecting the printer 59 to the data processor 52 may be an infrared ray, rather than an electric cord, taking an operation mode without a printer 59 into account. The printer 59 may be any printer which can print data to be indicated in the data indicator 53, but it may be set to print selected data.

The measuring apparatus of this embodiment allows data such as a measured value to be printed on a paper for storage, and also makes it possible that a patient with diabetes can use its printing function to print determination results on a paper, which the patient then brings to a physician for obtaining appropriate advice from the physician.

Embodiment 10

This embodiment relates to a measuring apparatus as shown in FIG. 10 further comprising an external storage 55, which will be described with reference to FIG. 11.

Figure 11:
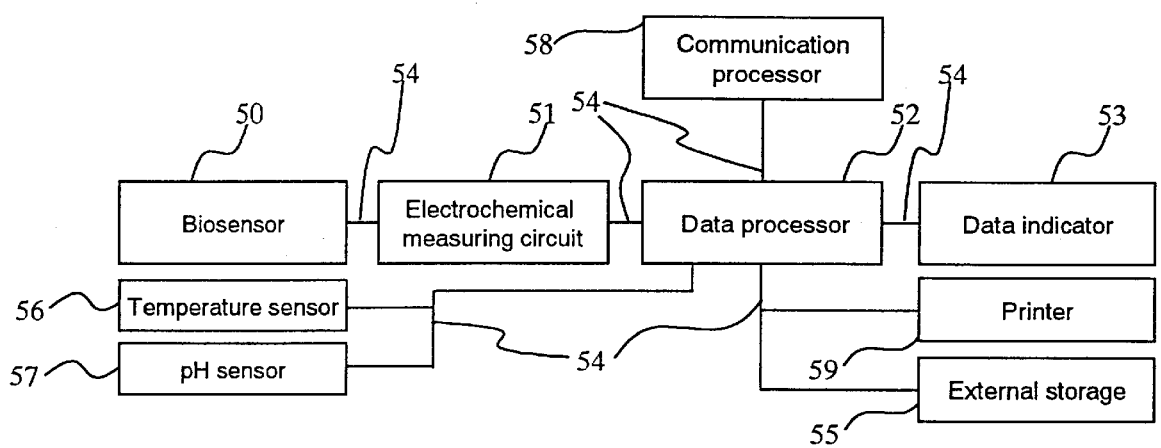
FIG. 11 shows another configuration example of a measuring apparatus according to this invention.

The measuring apparatus of this embodiment, as shown in FIG. 11, comprises a data processor 52 and an external storage which are mutually connected via a wiring 54. The external storage 55 may be a common storage medium; preferably magnetic storage media such as a floppy disk, semiconductor storage media such as a memory card, and optical storage media such as an optical disk because they are readily removed and inexpensive.

The measuring apparatus of this embodiment may be used to store measuring data on a storage medium, which a user can, as necessary, bring to a hospital. A physician in the hospital can analyze the stored measuring data to give an appropriate medical treatment to the patient with diabetes. Furthermore, a mass of measuring data can be stored for a long time. The apparatus is administered by means of passwords, so that patient's privacy can be protected and one apparatus may be used by two or more users. Data to be stored may be selected by setting as appropriate.

EXAMPLES

This invention will be specifically described with reference to Examples.

Example 1

Four devices were prepared, in which a silver/silver chloride electrode with an area of 1 mm$^2$ was formed on a 10 mm×6 mm quartz substrate.

Then, for each device, a different solution was applied by spin-coating on the silver/silver chloride electrode. Thus, four different reference electrodes described in the following (1) to (4) were prepared;

(1) an albumin layer was formed by applying a 22.5 w/v % solution of albumin containing 1 v/v % of glutaraldehyde by spin-coating;

(2) a reference electrode on which an acetyl cellulose was formed by applying a 2 w/v % solution of acetyl cellulose in acetone by spin-coating;

(3) a reference electrode on which a methacrylate-resin polyfluoroalcohol ester layer was formed by applying a 0.3 wt % solution of a methacrylate-resin polyfluoroalcohol ester in perfluorohexane by spin-coating; and (4) a reference electrode on which an acrylate-resin polyfluoroalcohol ester layer was formed by applying a 2.0 wt % solution of an acrylate-resin polyfluoroalcohol ester in xylene hexafluoride by spin-coating.

Spin-coating was conducted under the conditions of 3000 rpm and 30 sec. After spin-coating, an applied solution was dried to form a protection layer.

Glutaraldehyde, albumin, xylene hexafluoride and acetyl cellulose used were supplied by Wako Pure Chemicals, Co. Ltd. Acetone was supplied by Kanto Chemicals, Co. Ltd. The acrylate-resin polyfluoroalcohol ester was 1H,1H,2H, 2H-perfluorodecyl polyacrylate. The methacrylate-resin fluoroalcohol ester was Florard 722 (Sumitomo 3M), which was 1H,1H-perfluorooctyl polymethacrylate with an average molecular weight (Mn) of about 7000 as measured by GPC. Perfluorohexane as a diluent was Florard 726 (Sumitomo 3M).

Each of these four reference electrodes was evaluated for its continuous-operation life by determining its spontaneous-potential in an TES (N-tris(hydroxymethyl) methyl-2-aminoethanesulfonic acid) buffer, pH 7, containing 150 mM sodium chloride. A continuous-operation life was defined as a time until the spontaneous-potential became unstable.

Continuous-operation lives were about 24 hours and about 26 hours for the reference electrodes having an albumin layer and an acetyl cellulose layer, respectively, while at least about 2000 hours and at least about 2400 hours for the reference electrodes having a methacrylate-resin polyfluoroalcohol ester layer and an acrylate-resin polyfluoroalcohol ester, respectively.

Example 2

Four devices were prepared, in which a silver/silver chloride electrode with an area of 1 mm$^2$ was formed on a 10 mm×6 mm quartz substrate.

Then, for each device, a different solution was applied by spin-coating on the silver/silver chloride electrode, to form a different layer. Thus, reference electrodes described in the following (1) to (4) were prepared;

(1) an albumin layer was formed by applying a 22.5 w/v % solution of albumin containing 1 v/v % of glutaraldehyde by spin-coating;

(2) a reference electrode on which an acetyl cellulose was formed by applying a 2 w/v % solution of acetyl cellulose in acetone by spin-coating;

(3) a reference electrode on which a methacrylate-resin polyfluoroalcohol ester layer was formed by applying a 0.3 wt % solution of a methacrylate-resin polyfluoroalcohol ester in perfluorohexane by spin-coating; and (4) a reference electrode on which an acrylate-resin polyfluoroalcohol ester layer was formed by applying a 2.0 wt % solution of an acrylate-resin polyfluoroalcohol ester in xylene hexafluolide by spin-coating.

Spin-coating was conducted under the conditions of 3000 rpm and 30 sec. After spin-coating, an applied solution was dried to form a protection layer.

Glutaraldehyde was supplied by Wako Pure Chemicals, Co.Ltd and other reagents were as described in Example 1.

Each of these four reference electrodes was evaluated for its continuous-operation life by determining its spontaneous-potential in an TES (N-tris(hydroxymethyl) methyl-2-aminoethanesulfonic acid) buffer, pH 7, containing 150 mM sodium chloride. A continuous-operation life was defined as a time until the spontaneous-potential became unstable.

Continuous-operation lives were about 38 hours and about 48 hours for the reference electrodes having an albumin layer and an acetyl cellulose layer, respectively, while at least about 3400 hours for both of the reference electrodes having a methacrylate-resin polyfluoroalcohol ester layer and an acrylate-resin polyfluoroalcohol ester.

Example 3

On a 10 mm×6 mm quartz substrate was formed a silver/silver chloride electrode with an area of 1 mm$^2$, on which were then applied by spin-coating a 1 v/v % solution of γ-aminopropyltriethoxysilane and then a 0.3 wt % solution of a methacrylate-resin polyfluoroalcohol ester in perfluorohexane, to prepare a reference electrode having a methacrylate-resin polyfluoroalcohol ester layer. Spin-coating conditions in both application steps were 3000 rpm and 30 sec. Reagents used were as described in Example 1.

Figure 3:
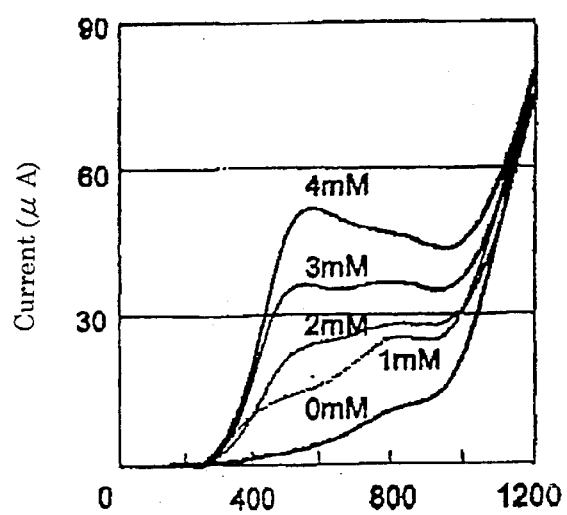
FIG. 3 shows properties for a reference electrode according to this invention.
Figure 3:
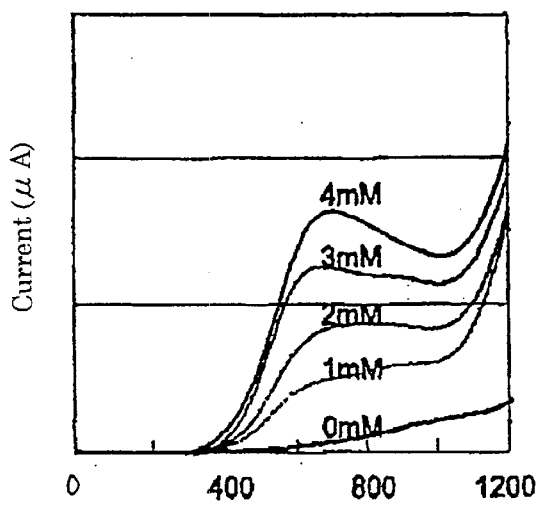
Figure 4:
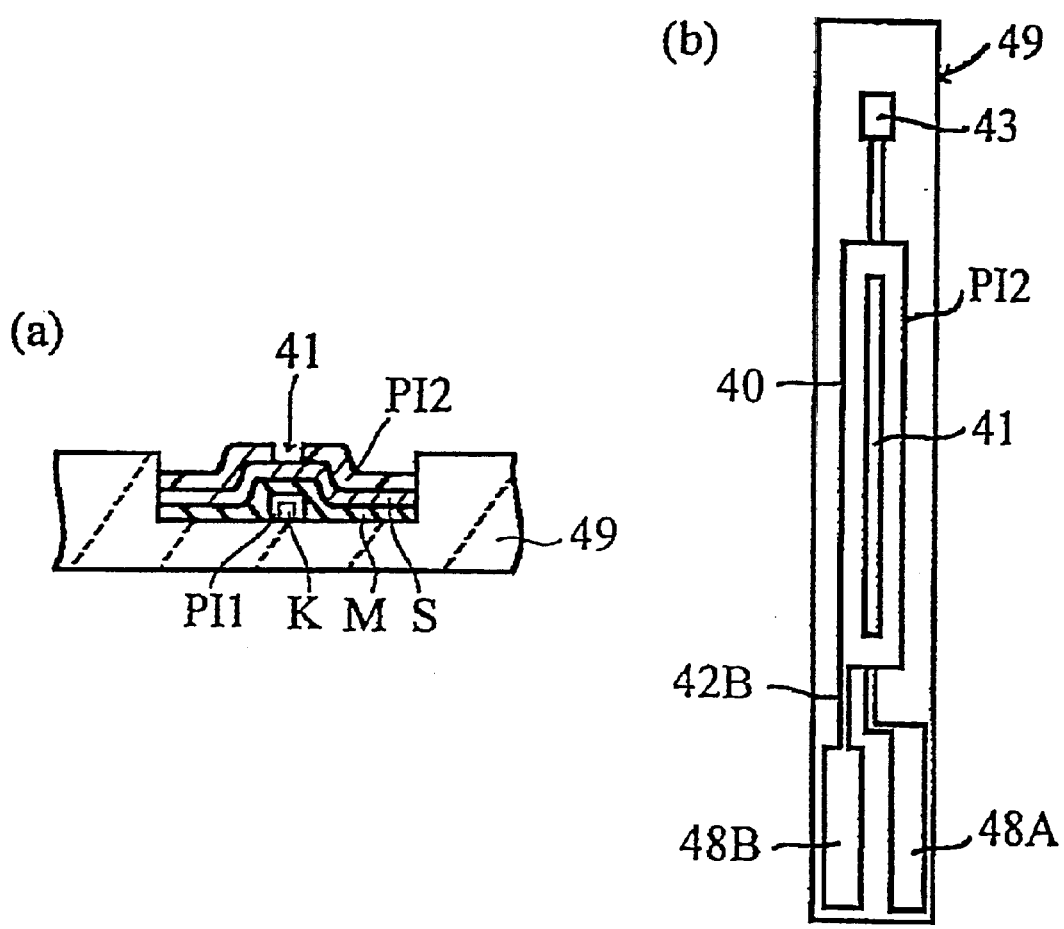
FIG. 4 shows a front view and a cross section for a biosensor (urinary-sugar sensor) according to the prior art.

The reference electrode was evaluated for its peak potential by determining current-potential characteristics in an TES (N-tris(hydroxymethyl)methyl-2-aminoethanesulfonic acid) buffer, pH 7, containing 150 mM sodium chloride. A working and a counter electrodes were a platinum electrode with an electrode area of 4 mm$^2$. An existing glass reference electrode as a control (Toa Denpa Kogyo, Co. Ltd.; GST-5422S) was also evaluated in a similar manner. Current-potential characteristics obtained are shown in FIG. 3 where the values from 0 to 4 mM are concentrations of hydrogen peroxide.

For the reference electrode according to this invention, a potential of to hydrogen peroxide had a peak near about 600 mV while for the existing reference electrode, near about 700 mV. The difference, 100 mV, between these peaks can be calculated using Nernst's equation (−59.16 mV/decade, $E_e=E^0+(RT/nF)\log a_0/a_r$). That is, it was almost correspondent to a potential for a concentration difference between 150 mM and 3.3 M of potassium chloride. Current-potential characteristics to hydrogen peroxide were identical between these electrodes except the above difference in a peak position.

Example 4

Two 10 mm×6 mm quartz substrates were prepared. On each substrate was formed a silver/silver chloride electrode with an area of 1 mm² and was then applied by spin-coating a 1 v/v % solution of γ-aminopropyltriethoxysilane. Spin-coating conditions were 3000 rpm and 30 sec.

A different solution was applied by spin-coating on each substrate. Thus, reference electrodes in the following (1) and (2) were prepared;

(1) a reference electrode on which a methacrylate-resin polyfluoroalcohol ester layer was formed by applying a 0.3 wt % solution of a methacrylate-resin polyfluoroalcohol ester in perfluorohexane by spin-coating; and (2) a reference electrode on which an acrylate-resin polyfluoroalcohol ester layer was formed by applying a 2.0 wt % solution of an acrylate-resin polyfluoroalcohol ester in xylene hexafluoride by spin-coating.

Spin-coating was conducted under the conditions of 3000 rpm and 30 sec. Reagents used were as described in Example 1.

These reference electrodes were evaluated for a decreasing rate of a spontaneous-potential to a chloride ion concentration in an TES (N-tris(hydroxymethyl)methyl-2-aminoethanesulfonic acid) buffer, pH 7, containing 150 mM sodium chloride, in comparison with a value of −59.16 mV obtained from Nernst's equation.

For the reference electrodes of this invention, a spontaneous-potential was reduced, with respect to a 50 to 500 mM of chloride ion concentration, at a rate of −59.4 mV/decade for the reference electrode having a methacrylate-resin polyfluoroalcohol ester and at a rate of −59.0 mV/decade for the reference electrode having an acrylate-resin polyfluoroalcohol ester. These values were well correspondent to Nernst's equation, indicating that the electrodes satisfactorily functioned as a reference electrode.

Example 5

Six devices were prepared, in which a silver/silver chloride electrode with an area of 1 mm² was formed on a 10 mm×6 mm quartz substrate.

Then, on the silver/silver chloride electrode was applied by spin-coating a 1 v/v % solution of γ-aminopropyltriethoxysilane to form a γ-aminopropyltriethoxysilane layer. Then, reference electrodes described in the following (1) to (3) were prepared;

(1) a reference electrode having a protection layer of 1H,1H-perfluorooctyl polymethacrylate by applying a 0.3 wt % solution of 1H,1H-perfluorooctyl polymethacrylate in perfluorohexane on the γ-aminopropyltriethoxysilane layer by spin-coating;

(2) a reference electrode having a protection layer of 1H,1H2H,2H-perfluorodecyl polyacrylate by applying a 2 wt % solution of 1H,1H,2H,2H-perfluorodecyl polyacrylate in xylene hexafluoride on the γ-aminopropyltriethoxysilane layer by spin-coating; and (3) a reference electrode having a protection layer comprising cyclohexyl polymethacrylate and 1H,1H,2H,2H-perfluorodecyl polyacrylate by applying a mixed solution of 2 wt % 1H,1H,2H,2H-perfluorodecyl polyacrylate and 2 wt % cyclohexyl polymethacrylate in xylene hexafluoride on the γ-aminopropyltriethoxysilane layer by spin-coating.

Spin-coating was conducted under the conditions of 3000 rpm and 30 sec. These three types of reference electrodes were separately evaluated for their continuous operation lives by determining their spontaneous-potential in an TES (N-tris(hydroxymethyl)methyl-2-aminoethanesulfonic acid) buffer, pH 7, containing 150 mM sodium chloride at 25° C. and 50° C. A continuous-operation life was defined as a time until the spontaneous-potential became unstable.

Continuous-operation lives were 2000 hours at 25° C. and 10 hours at 50° C. for the reference electrode having a 1H,1H-perfluorooctyl polymethacrylate layer while 2400 hours at 25° C. and 1200 hours at 50° C. for the reference electrode having a 1H,1H,2H,2H-perfluorodecyl polyacrylate layer. The reference electrode having a 1H,1H,2H,2H-perfluorodecyl polyacrylate layer containing cyclohexyl polymethacrylate gave lives of 3000 hours at 25° C. and 2800 hours at 50° C., Example 6

This example relates to an example of a measuring apparatus having the configuration shown in FIG. 6.

First, there will be described a procedure for manufacturing a biosensor unit in the measuring apparatus of this example. On a 10 mm×6 mm quartz substrate was formed a silver/silver chloride electrode with an area of 1 mm². Then, on the overall surface were sequentially applied by spin coating a 1 v/v % solution of γ-aminopropyltriethoxysilane to form a binding layer; and a mixed solution of 2 wt % 1H,1H,2H,2H-perfluorodecyl polyacrylate and 2 wt % cyclohexyl polymethacrylate in xylene hexafluoride to prepare a reference electrode having a 1H,1H,2H,2H-perfluorodecyl polyacrylate layer containing cyclohexyl polymethacrylate. Spin-coating in any application was conducted under the conditions of 3000 rpm and 30 sec.

Separately from the above substrate having a reference electrode, a 10 mm×6 mm quartz substrate was prepared, on which were formed a working electrode of platinum (area: 7 mm²) and a counter electrode (area: 4 mm²). Then, on the overall surface were sequentially applied by spin coating a 1 v/v % solution of γ-aminopropyltriethoxysilane to form a binding layer; a 22.5 w/v % solution of albumin containing 56.5 U/μL glucose oxidase and 1 v/v % glutaraldehyde to form an immobilized enzyme layer; and a 1.7 wt % solution of an acrylate-resin polyfluoroalcohol ester to form a permeation restricting layer. The acrylate-resin polyfluoroalcohol ester was 1H,1H2H,2H-perfluorodecyl polyacrylate. The diluent was hexafluoroxylene. The conditions of spin-coating were 3000 rpm and 30 sec.

Using a biosensor comprising an electrode unit thus manufactured, a measuring apparatus having a configuration shown in FIG. 6 was manufactured, where the electrode unit was connected, via wire bonding, with a flexible substrate, which was connected with an electrochemical measuring circuit via a pin-jack type wiring.

The electrochemical measuring circuit was a potentiostat, HOKUTODENKOPOTENTIOSTAT/

GALVANOSTATHA150G (Hokuto Denko). The data processor was a personal computer, PC-9821RaII23 (NEC corporation). The data indicator 53 was a display, PC-KP531 (NEC corporation). The electrochemical measuring circuit, the data processor and the data indicator 53 were mutually connected via a pin-jack type wiring.

Operation of the measuring apparatus of this example will be described. An operator soaked the above electrode unit into a buffer of 1 mM TES (N-tris(hydroxymethyl)methyl-2-aminoethanesulfonic acid), pH 7, containing sodium chloride at 150 mM, and turned the apparatus on. Then, the data indicator displayed a message "Time setting; Enter a current time". According to the indication, the operator entered the current time by key operation, and then the data indicator displayed the message "A current time was entered". When an entered time was incorrect, the message "Time setting; Enter a current time" is displayed. Thus, the entered current time is stored in the data processor.

Then, the data indicator displayed a message "Standby mode. Please wait.". After a current from the electrode, the data indicator displayed a message "Calibration; Soak the electrode into a calibration solution". According to the indication, the operator soaked the electrode unit into a calibration solution of 200 mg/dL glucose for calibration. Then, the data indicator displayed a message "Calibration was normally finished. After washing, resoak the electrode into the buffer.". Whether the calibration has been normally conducted is judged by the data processor and the result is displayed on the data indicator. If the calibration is not normally conducted, a message "Not calibrated. After washing the electrode, resoak it into the calibration solution" or "The electrode is broken. Replace it." is displayed. After the calibration, the operator soaked the electrode unit into the buffer for measurement. When the electrode is not returned into the buffer 10 sec after the calibration is completed, an alarm sounds.

Then, the operator selected the item "Start measurement" displayed on the data indicator, and then the indicator displayed a message "Measurement will be started. Soak the electrode into an urine sample.". According the indication, the operator soaked the electrode unit into an urine sample to initiate measurement. Ten seconds after the measurement initiation, the data indicator displayed a message "Measurement has been normally finished. An urinary-sugar concentration is . . . mg/dL.". Whether the measurement has been normally conducted is judged by the data processor and the result is displayed on the data indicator. If the measurement is not normally conducted, a message "Not measured. After washing the electrode, resoak it into the urine solution" or "The electrode is broken. Replace it." is displayed.

After the measurement, the data indicator displayed a message "Wash and resoak the electrode into the buffer". When the electrode is not returned into the buffer 10 sec after the measurement is completed, an alarm sounds. Then, the operator selected the item "Completion of measurement" on the data indicator, to complete the measurement.

For the measuring apparatus of this example, a measuring time may be set in advance. At the set time, an indicating sound generates while the data indicator displays a message "Measurement will be started. Soak the electrode into an urine sample.". The time may be set as appropriate and a plurality of times may be set.

After entering data in the data processor in the measuring apparatus of this invention, an indicating sound is generated in either case that the entry is acceptable or unacceptable. An indicating light rather than an indicating sound may be employed. When an abnormal current is detected between the biosensor, the electrochemical measuring circuit, the data processor and the wiring, an abnormal-current indicator displays a message "An abnormal current was detected" on the data indicator. Displaying the message may prevent failure of the apparatus.

Since all of the biosensor, the electrochemical measuring circuit and the data processor are connected via a pin-jack type wiring, they are readily removed and may be replaced as necessary.

As described above, the measuring apparatus of this example may be used to regularly conduct measurement at a given time without misoperation and anyone can easily operate it.

Example 7

This example relates to an example of a measuring apparatus having a configuration shown in FIG. 8. The measuring apparatus is the apparatus shown in FIG. 6 further comprising a pH sensor and a temperature sensor.

The temperature sensor was a thermocouple type and the pH sensor was an ion-sensitive field effect transistor type. The pH sensor, the temperature sensor, the electrochemical measuring circuit, the data processor and the data indicator were mutually connected via an electric wire.

Operation of the measuring apparatus of this example will be described. An operator soaked the electrode unit into a buffer of 1 mM TES (N-tris(hydroxymethyl)methyl-2-aminoethanesulfonic acid), pH 7, containing sodium chloride at 150 mM, and turned the apparatus on. After 1 min, the base current of the electrode became stable. In this state, the electrode was soaked into a 200 mg/dL standard solution of glucose for calibration. Since the glucose standard solution contains a pH indicator, the pH sensor can be calibrated at the same time. Except replacement of the electrode, the apparatus may be kept power-ON as long as the electrode is connected.

Then, the operator selected the item "Start measurement", and the data indicator displayed a message "Measurement will be started. Soak the electrode into an urine sample.".

According the indication, the operator sequentially measured an urinary-sugar concentration for samples from two diabetic subjects once per a sample. During the measurement, a memo registration means was used to enter a blood pressure and a temperature at the same time for each subject. Then, 10 sec. after the first subject soaked the electrode unit into urine, the data indicator displayed a message "Measurement has been normally finished. An urinary-sugar concentration is 80 mg/dL." and a voice message "Measurement has been normally finished. An urinary-sugar concentration is 80 mg/dL." sounded. After 20 sec, the second subject soaked the electrode unit into urine. After 10 sec, the data indicator displayed a message "Measurement has been normally finished. An urinary-sugar concentration is 180 mg/dL." and a voice message "Measurement has been normally finished. An urinary-sugar concentration is 180 mg/dL." sounded. These results were compared with those obtained from an existing laboratory apparatus (Hitachi Automatic Analyzer 7050 according to a glucose dehydrogenase technique). There were good matching and a higher correlation between the measurements.

Thus, the measuring apparatus of this example may be used to sequentially detect an urinary-sugar concentration for two subjects. Even a subject with a weak eyesight could reliably determine his/her urinary-sugar concentration. In addition, the memo-registration means could be used to access a temperature and a blood pressure entered in advance. It allowed an operator to compare these values to the urinary-sugar concentration for carefully administrating subject's conditions. Furthermore, the measured values were corrected for a temperature and a pH, so that highly precise detection comparable to an existing laboratory apparatus could be conducted.

Example 8

This example relates to an example of a measuring apparatus having a configuration shown in FIG. 9. This measuring apparatus is the apparatus in FIG. 8 further comprising a communication processor 58. The communication processor 58 was a modem-terminal adapter, PC-IT65S1P (NEC corporation). The pH sensor, the temperature sensor, the electrochemical measuring circuit, the data processor, the data indicator and the communication processor were mutually connected via an electric wire.

This apparatus was used to detect an urinary-sugar concentration for one diabetic twice (2 hours after breakfast and dinner) a day for 30 days. A measured value was sent to a hospital via a telephone line one by one.

Thus, the patient successfully observed the measuring times, so that the hospital could plot the received data into a graph and analyze it for appropriately administrating the patient's conditions.

Example 9

This example relates to an example of a measuring apparatus having a configuration shown in FIG. 10. The measuring apparatus is the apparatus in FIG. 9 further comprising a printer 59. The printer 59 was a laser printer, Multiwriter 2000X (NEC corporation). The printer was connected with the data processor via a printer cable, PC-CA202. There will be described measurement results using the measuring apparatus of this example.

This apparatus was used to detect an urinary-sugar concentration for consecutive 100 diabetics. The apparatus was calibrated only once when starting it. For the same samples, an urinary-sugar concentration was detected with an existing laboratory apparatus (Hitachi Automatic Analyzer 7050 according to a glucose dehydrogenase technique), whose results were compared with those from the measuring apparatus of this example. Then, a coefficient of correlation obtained was 0.96 and a regression formula was Y=1.09X+ 88. It was shown that the apparatus of this example could conduct detection with a precision comparable to that in the existing laboratory apparatus. A measuring time for the apparatus of this example was as short as about 90 sec per a sample, allowing an operator to quickly conduct detection. Furthermore, the apparatus of this example was equipped with the printer 59, so that the measurement results could be quickly printed for confirmation. The patient could show a physician the printed results in a hospital for receiving his/her advice.

Example 10

This example relates to an example of a measuring apparatus having a configuration shown in FIG. 11. The measuring apparatus is the apparatus shown in FIG. 10 further comprising an external storage 55. The external storage was a 3.5 inch optical disk unit, PC-OD302R (NEC corporation). The external storage was connected with the data processor via an electric wire. Operation of the measuring apparatus of this example will be described.

An operator soaked the electrode unit into a buffer of 1 mM TES (N-tris(hydroxymethyl)methyl-2-aminoethanesulfonic acid), pH 7, containing sodium chloride at 150 mM, and turned the apparatus on. After about 1 min, the base current of the electrode became stable. In this state, the electrode was soaked into a 200 mg/dL standard solution of glucose for calibration and the enzyme electrode was calibrated.

Then, the operator selected an item "Entry of the number of subjects" displayed on the data indicator, and a message "Enter the number of subjects" was displayed. After the operator entered the number of subjects according to this instruction, the data indicator displayed a message " . . . subjects will be tested.(Yes, Y/No. N)". "Yes, Y" was selected and then a message " . . . subjects can be tested" was displayed. If "No, N" is selected, the message "Enter the number of subjects" is again displayed and the above procedure is repeated until "Yes, Y" is selected.

The operator selected an item "Password" on the data indicator and then "Registration of a password". The data processor recognizes that the password entering button has been pushed to make the data indicator display a message "A password will be registered. Enter a 4 digit number.". After the operator entered a 4 digit number according to this instruction, the data indicator displayed a message "Enter the same password". After the operator entered the same number again, a message "The password was received" was displayed. Passwords are registered by the number of subjects. Thus, the registered passwords are stored in the memory in the data processor.

Then, the data indicator displayed a message "Measurement will be started. After entering the password, soak the electrode into an urine sample.". According to this instruction, the operator entered the password and soak the electrode into urine to start detection. Then, the data indicator displayed a message "Measurement has been normally finished. An urinary-sugar concentration is . . . mg/dL.". If the measurement is not normally conducted, a message "Not measured. After washing the electrode, resoak it into the urine solution" or "The electrode is broken. Replace it." is displayed. If a correct password is not entered, the message "Measurement will be started. After entering the password, soak the electrode into an urine sample." is again displayed. If an incorrect password is entered three consecutive times, all the measured data are deleted and the setting returns to the initial state.

After normally completing detection, the data indicator displayed a message "Wash and resoak the electrode into the buffer".

The operator selected "Memo registration" on the data indicator and then a message "A memo is registered? (Yes, Y/No, N)" was displayed. After selecting "Y", a message "Enter the password" was displayed. The operator entered the password and memo data, and then the data indicator displayed the message "A memo is registered? (Yes, Y/No, N)". The operator selected "Y" and entered the memo data, and then the data indicator again displayed the message "A memo is registered? (Yes, Y/No, N)". The operator selected "Y" and registered the memo. For stopping the input process, "N" is selected. When reading, amending or deleting a registered memo, a message "After entering the password, designate the memo number." is displayed. According to the instruction, the operator can enter the password to read, amend or delete the memo. If an incorrect password is entered, a message "The password is incorrect. Enter the password again." is displayed. If an incorrect password is entered three consecutive times, all the memo data are deleted and the setting returns to the initial state.

Measurement results obtained using the measuring apparatus of this example will be described. The apparatus of this example was used to repeatedly measure an urinary-sugar concentration for two diabetics twice a day for a week. The apparatus was calibrated only once when starting it. For the same samples, an urinary-sugar concentration was detected with an existing laboratory apparatus (Hitachi Automatic Analyzer 7050 according to a glucose dehydrogenase technique), whose results were compared with those from the measuring apparatus of this example. Then, a coefficient of correlation obtained was 0.955 (n=28). It was shown that the apparatus of this example could conduct detection with a precision comparable to that in the existing laboratory apparatus. Since the memo function was used to enter the names of the patients, the measurement data were not mixed up. Since passwords were used for data management, patient's privacy could be protected during measurement. The measurement data could be graphically represented. Furthermore, the optical disk storing the data was portable, so that the data could be managed or analyzed by another PC.

As described above, a reference electrode according to this invention or a biosensor therewith comprises a protection layer mainly consisting of a polymer having a particular structure on an electrode, so that it may provide. the following effects.

1) Its life and stability during operation may be significantly increased because the electrode is covered by the protection layer to prevent metal materials composing the electrode from eluting into an electrolyte. For example, when the electrode is a silver/silver chloride electrode, dissociation of silver chloride or elution of silver ion can be prevented.

2) Adhesion of contaminants to the surface of the reference electrode is sufficiently inhibited to give stable sensitivity even after long-term operation because the reference electrode comprises a protection layer having a particular structure which may prevent contaminants from adhering to the surface.

3) The reference electrode or the biosensor can be manufactured in a smaller size than that according to the prior art, with less restrictions to its shape than the prior art, because the reference electrode of this invention does not require a solution of potassium chloride, a space for storing the solution, an injection port for the solution or a liquid junction within the electrode.

4) It can be mass-produced at a lower cost because the main manufacturing process consists of forming an electrode by, e.g., spattering and forming, e.g., a protection layer by spin-coating so that majority of existing processes for manufacturing a semiconductor can be utilized as they are.

5) The reference electrode is improved in strength, so it can be easily handled because the protection layer formed on the surface of the reference electrode according to this invention is improved in strength and is mainly composed of a polymer having a particular structure which is excellently adhesive to, e.g., the electrode.

The biosensor of this invention may be used to determine an urinary-sugar concentration undetectable with a conventional sensor for an individual whose urinary-sugar concentration is normal or a prediabetic individual, making it possible to collect data useful in prophylaxis for diabetes.

In this manufacturing process, a protection layer is formed by applying and then drying a liquid comprising a polymer component having a particular structure. Thus, there may be provided, with a good controllability for a film thickness, a protection layer which is excellent in stability for repeated measurement, adhesiveness to adjacent layers and durability.

What is claimed is:

1. A reference electrode comprising an electrode on an insulating substrate and a protection layer covering the electrode, said protection layer consisting essentially of a polymer in which a pendant group containing at least a fluoroalkylene block is attached to a non-fluorinated vinyl polymer;

wherein the vinyl polymer is a homopolymer or copolymer of one or more monomers selected from the group consisting of unsaturated hydrocarbons, unsaturated carboxylic acids and unsaturated alcohols.

2. The reference electrode as claimed in claim 1, further comprising a binding layer consisting essentially of a silane-coupling agent between the electrode and the protection layer.

3. A biosensor equipped with a reference electrode as claimed in claim 1.

4. A measuring apparatus comprising the biosensor as claimed in claim 3 and a data indicator indicating an electric signal from the biosensor.

5. A measuring apparatus comprising the biosensor as claimed in claim 3; an electrochemical measuring circuit receiving an electric signal from the biosensor; a data processor calculating a measured value based on the electric signal; and a data indicator indicating the measured value.

6. The measuring apparatus as claimed in claim 5 where the data processor comprises all or some of the following means;

(a) a timer;

(b) a time setting means for setting a time and a time indicator indicating a time at the time set by the time setting means;

(c) an operation guide means describing operation instructions for the measuring apparatus;

(d) a measured-value storing means for storing a calculated measured value;

(e) a password registration means for registering a password for a user of the measuring apparatus;

(f) a memo registration means for registering a memo;

(g) an operation indicator for detecting malfunction in the measuring apparatus;

(h) a calibration-timing indicator for detecting and indicating a calibration timing for the biosensor;

(i) an electrode-replacement-timing indicator for detecting and indicating a replacement timing for the electrode in the biosensor;

(j) an abnormal-current indicator for detecting and indicating an abnormal current; and (k) a calibrator for calibrating the biosensor.

7. A reference electrode comprising an electrode on an insulating substrate and a protection layer covering the electrode, said protection layer consisting essentially of a polymer in which a pendant group containing at least a fluoroalkylene block is attached to a non-fluorinated vinyl polymer;

wherein the vinyl polymer is a polycarboxylic acid.

8. A reference electrode comprising an electrode on an insulating substrate and a protection layer covering the electrode, said protection layer consisting essentially of a polymer in which a pendant group containing at least a fluoroalkylene block is attached to a non-fluorinated vinyl polymer;

wherein the fluoroalkylene block is attached to the vinyl polymer via an ester group.

9. A reference electrode comprising an electrode on an insulating substrate and a protection layer covering the electrode, said protection layer consisting essentially of a polymer in which a pendant group containing at least a fluoroalkylene block is attached to a non-fluorinated vinyl polymer;

wherein the fluorine content represented by x/(x+y) in the pendant group is 0.3 to 1, where x and y are the numbers of fluorine and hydrogen atoms in the pendant group, respectively.

10. A reference electrode comprising an electrode on an insulating substrate and a protection layer covering the electrode, said protection layer consisting essentially of a polymer in which a pendant group containing at least a fluoroalkylene block is attached to a non-fluorinated vinyl polymer;

wherein the pendant group has 3 to 15 carbon atoms.

11. A reference electrode comprising an electrode on an insulating substrate and a protection layer covering the electrode, said protection layer consisting essentially of a polycarboxylic acid (A) fluoroalcohol ester.

12. The reference electrode as claimed in claim 11 where the polycarboxylic acid (A) is polymethacrylic acid, polyacrylic acid or a copolymer of acrylic acid and methacrylic acid.

13. The reference electrode as claimed in claim 11 where the fluorine content represented by x/(x+y) in the polycarboxylic acid (A) fluoroalcohol ester is 0.3 to 1, where x and y are the numbers of fluorine and hydrogen atoms in the fluoroalcohol ester, respectively.

14. The reference electrode as claimed in claim 11 where the fluoroalcohol moiety in the polycarboxylic acid (A) fluoroalcohol ester has 3 to 15 carbon atoms.

15. The reference electrode as claimed in claim 11 where the fluoroalcohol moiety in the polycarboxylic acid (A) fluoroalcohol ester is derived from a primary alcohol.

16. The reference electrode as claimed in claim 11 where the polycarboxylic acid (A) fluoroalcohol ester is 1H,1H-perfluorooctyl polymethacrylate.

17. The reference electrode as claimed in claim 11 where the polycarboxylic acid (A) fluoroalcohol ester is 1H,1H,2H,2H-perfluorodecyl polyacrylate.

18. The reference electrode as claimed in claim 11 where the electrode is a silver/silver chloride electrode.

19. The reference electrode as claimed in claim 11 where the protection layer has a thickness of 0.01 to 3 $\mu$m.

20. The reference electrode as claimed in claim 11 further comprising a binding layer mainly consisting of a silane-coupling agent between the electrode and the protection layer.

21. A biosensor equipped with a reference electrode as claimed in claim 11.

22. A measuring apparatus comprising the biosensor as claimed in claim 21 and a data indicator indicating an electric signal from the biosensor.

23. A measuring apparatus comprising the biosensor as claimed in claim 21; an electrochemical measuring circuit receiving an electric signal from the biosensor; a data processor calculating a measured value based on the electric signal; and a data indicator indicating the measured value.

24. The measuring apparatus as claimed in claim 23 where the data processor comprises all or some of the following means;

(a) a timer;
(b) a time setting means for setting a time and a time indicator indicating a time at the time set by the time setting means;
(c) an operation guide means describing operation instructions for the measuring apparatus;
(d) a measured-value storing means for storing a calculated measured value;
(e) a password registration means for registering a password for a user of the measuring apparatus;
(f) a memo registration means for registering a memo;
(g) an operation indicator for detecting malfunction in the measuring apparatus;
(h) a calibration-timing indicator for detecting and indicating a calibration timing for the biosensor;
(i) an electrode-replacement-timing indicator for detecting and indicating a replacement timing for the electrode in the biosensor;
(j) an abnormal-current indicator for detecting and indicating an abnormal current; and
(k) a calibrator for calibrating the biosensor.

25. A reference electrode comprising an electrode on an insulating substrate and a protection layer covering the electrode, said protection layer consisting essentially of a polycarboxylic acid (A) fluoroalcohol ester and a polycarboxylic acid (B) alkylalcohol ester.

26. The reference electrode as claimed in claim 25 where the polycarboxylic acid (B) is polymethacrylic acid, polyacrylic acid or a copolymer of acrylic acid and methacrylic acid.

27. The reference electrode as claimed in claim 25 where the polycarboxylic acid (B) alkylalcohol ester is the polycarboxylic acid (B) whose carboxyl groups are at least partially esterified with an alkylalcohol having 2 to 10 carbon atoms.

28. The reference electrode as claimed in claim 25 where the polycarboxylic acid (B) alkylalcohol ester is cyclohexyl polymethacrylate.

29. The reference electrode as claimed in claim 25 where the polycarboxylic acid (A) is polymethacrylic acid, polyacrylic acid or a copolymer of acrylic acid and methacrylic acid.

30. The reference electrode as claimed in claim 25 where the fluorine content represented by x/(x+y) in the polycarboxylic acid (A) fluoroalcohol ester is 0.3 to 1, where x and y are the numbers of fluorine and hydrogen atoms in the fluoroalcohol ester, respectively.

31. The reference electrode as claimed in claim 25 where the fluoroalcohol moiety in the polycarboxylic acid (A) fluoroalcohol ester has 3 to 15 carbon atoms.

32. The reference electrode as claimed in claim 25 where the fluoroalcohol moiety in the polycarboxylic acid (A) fluoroalcohol ester is derived from a primary alcohol.

33. The reference electrode as claimed in claim 25 where the polycarboxylic acid (A) fluoroalcohol ester is 1H,1H-perfluorooctyl polymethacrylate.

34. The reference electrode as claimed in claim 25 where the polycarboxylic acid (A) fluoroalcohol ester is 1H,1H,2H,2H-perfluorodecyl polyacrylate.

35. The reference electrode as claimed in claim 25 where the electrode is a silver/silver chloride electrode.

36. The reference electrode as claimed in claim 25 where the protection layer has a thickness of 0.01 to 3 $\mu$m.

37. The reference electrode as claimed in claim 25 further comprising a binding layer mainly consisting of a silane coupling agent between the electrode and the protection layer.

38. A biosensor equipped with a reference electrode as claimed in claim 25.

39. A measuring apparatus comprising the biosensor as claimed in claim 38 and a data indicator indicating an electric signal from the biosensor.

40. A measuring apparatus comprising the biosensor as claimed in claim 38, an electrochemical measuring circuit receiving an electric signal from the biosensor; a data processor calculating a measured value based on the electric signal; and a data indicator indicating the measured value.

41. The measuring apparatus as claimed in claim 40 where the data processor comprises all or some of the following means;
   (a) a timer;
   (b) a time setting means for setting a time and a time indicator indicating a time at the time set by the time setting means;
   (c) an operation guide means describing operation instructions for the measuring apparatus;
   (d) a measured-value storing means for storing a calculated measured value;
   (e) a password registration means for registering a password for a user of the measuring apparatus;
   (f) a memo registration means for registering a memo;
   (g) an operation indicator for detecting malfunction in the measuring apparatus;
   (h) a calibration-timing indicator for detecting and indicating a calibration timing for the biosensor;
   (i) an electrode-replacement-timing indicator for detecting and indicating a replacement timing for the electrode in the biosensor;
   (j) an abnormal-current indicator for detecting and indicating an abnormal current; and
   (k) a calibrator for calibrating the biosensor.

42. A reference electrode comprising an electrode on an insulating substrate and a protection layer covering the electrode, said protection layer consisting essentially of a polycarboxylate comprising alkylalcohol ester and fluoroalcohol ester groups.

43. The reference electrode as claimed in claim 42 where the fluorine content represented by $x/(x+y)$ in the fluoroalcohol ester group is 0.3 to 1, where x and y are the numbers of fluorine and hydrogen atoms in the fluoroalcohol ester group, respectively.

44. The reference electrode as claimed in claim 42 where the fluoroalcohol moiety in the fluoroalcohol ester group has 3 to 15 carbon atoms.

45. The reference electrode as claimed in claim 42 where the fluoroalcohol moiety in the fluoroalcohol ester group is derived from a primary alcohol.

46. The reference electrode as claimed in claim 42 where the fluoroalcohol ester group is 1H,1H-perfluorooctyl polymethacrylate group.

47. The reference electrode as claimed in claim 42 where the fluoroalcohol ester group is 1H,1H,2H,2H-perfluorodecyl polyacrylate group.

48. The reference electrode as claimed in claim 42 where the alkylalcohol ester group has 2 to 10 carbon atoms.

49. The reference electrode as claimed in claim 42 where the alkylalcohol ester group is cyclohexyl polymethacrylate group.

50. The reference electrode as claimed in claim 42 where the electrode is a silver/silver chloride electrode.

51. The reference electrode as claimed in claim 42 where the protection layer has a thickness of 0.01 to 3 $\mu$m.

52. The reference electrode as claimed in claim 42 further comprising a binding layer mainly consisting of a silane-coupling agent between the electrode and the protection layer.

53. A biosensor equipped with a reference electrode as claimed in claim 42.

54. A measuring apparatus comprising the biosensor as claimed in claim 53 and a data indicator indicating an electric signal from the biosensor.

55. A measuring apparatus comprising the biosensor as claimed in claim 53, an electrochemical measuring circuit receiving an electric signal from the biosensor; a data processor calculating a measured value based on the electric signal; and a data indicator indicating the measured value.

56. The measuring apparatus as claimed in claim 55 where the data processor comprises all or some of the following means;
   (a) a timer;
   (b) a time setting means for setting a time and a time indicator indicating a time at the time set by the time setting means;
   (c) an operation guide means describing operation instructions for the measuring apparatus;
   (d) a measured-value storing means for storing a calculated measured value;
   (e) a password registration means for registering a password for a user of the measuring apparatus;
   (f) a memo registration means for registering a memo;
   (g) an operation indicator for detecting malfunction in the measuring apparatus;
   (h) a calibration-timing indicator for detecting and indicating a calibration timing for the biosensor;
   (i) an electrode-replacement-timing indicator for detecting and indicating a replacement timing for the electrode in the biosensor;
   (j) an abnormal-current indicator for detecting and indicating an abnormal current; and
   (k) a calibrator for calibrating the biosensor.

57. A reference electrode comprising an electrode on an insulating substrate and a protection layer covering the electrode, said protection layer consisting essentially of a polymer in which a pendant group containing at least a fluoroalkylene block is attached to a non-fluorinated vinyl polymer;
   wherein the electrode is a silver/silver chloride electrode.

58. A method for manufacturing a reference electrode comprising the steps of: forming an electrode on an insulating substrate; and applying a liquid containing a polymer in which a pendant group having at least a fluoroalkylene block is attached to a non-fluorinated vinyl polymer, to the electrode directly or via another layer and then drying it to form a protection layer.

59. The method for manufacturing a reference electrode as claimed in claim 58 where after forming the electrode, a binding layer mainly consisting of a silane-coupling agent is formed before forming the protection layer.

60. The method for manufacturing a reference electrode as claimed in claim 58 where the liquid containing the polymer is applied by spin-coating.

61. The method for manufacturing a reference electrode as claimed in claim 58 where the liquid containing the polymer is applied by dip-coating and then the substrate is dried by nitrogen blowing.

62. The method for manufacturing a reference electrode as claimed in claim 58 where the protection layer has a thickness of 0.01 to 3 $\mu$m after drying.

* * * * *